(12) United States Patent
Cohen et al.

(10) Patent No.: US 10,857,170 B1
(45) Date of Patent: Dec. 8, 2020

(54) MOLECULES, COMPOSITIONS AND METHODS FOR MODULATION OF SIRT6

(71) Applicant: SirTLab Corporation, Ramat HaSharon (IL)

(72) Inventors: Haim Yosef Cohen, Modiin (IL); Yariv Kanfi, Petah Tiqwa (IL)

(73) Assignee: SirTLab Corporation, Ramat HaSharon (IL)

( * ) Notice: Subject to any disclaimer, the term of this patent is extended or adjusted under 35 U.S.C. 154(b) by 408 days.

(21) Appl. No.: 15/395,049

(22) Filed: Dec. 30, 2016

Related U.S. Application Data

(60) Provisional application No. 62/274,050, filed on Dec. 31, 2015.

(51) Int. Cl.
*A61K 31/7048* (2006.01)
*A61K 31/428* (2006.01)

(52) U.S. Cl.
CPC ........ *A61K 31/7048* (2013.01); *A61K 31/428* (2013.01)

(58) Field of Classification Search
CPC .................... A61K 31/7048; A61K 31/428
See application file for complete search history.

(56) References Cited

U.S. PATENT DOCUMENTS

2011/0105477 A1   5/2011   Carlson

OTHER PUBLICATIONS

Stohr et al. "ITCH modulates SIRT6 and SREBP2 to influence lipid metabolism and atherosclerosis in ApoE null mice" Scientific Reports, 2015, vol. 5, Article 9023.*
Masri et al., "Partitioning Circadian Transcription by SIRT6 Leads to Segregated Control of Cellular Metabolism" Cell. Jul. 31, 2014; 158(3): 659-672.
UCI News Jul. 31, 2014 "Strict genomic partitioning by biological clock separates key metabolic functions" (http://news.uci.edu/press-releases/strict-genomic-partitioning-by-biological-clock-separates-key-metabolic-functions/) (2 pages).
Cell Reports, vol. 29, Issue 12, Dec. 17, 2019, pp. 4127-43.
Cell Metabolism, vol. 12, Issue 3, Sep. 8, 2010, pp. 224-36.
Cell Reports, vol. 14, Issue 2, Jan. 12, 2016, pp. 234-42.
Cell Reports, vol. 4, Issue 5, Sep. 12, 2013, pp. 905-12.
Aging Cell, (2010) 9, pp. 162-73.
Aging 2018, vol. 10, No. 9, pp. 2394-2406.
Journal of Lipid Research, vol. 54, 2013, pp. 2745-2753.
Diabetes, vol. 66, Oct. 2017, pp. 2659-2668.
Molecular Metabolism, vol. 4, Issue 11, Nov. 2015, pp. 846-856.
Journal of Neurochemistry, 2018, 144, pp. 128-138.
International Journal of Oncology, 2019, 55, pp. 103-115.
PLOS One, Jun. 1, 2014, vol. 9, Issue 6, e98831, pp. 1-9.
PLOS One, Apr. 27, 2017, pp. 1-15.
Cell, 140, Jan. 22, 2010, pp. 280-293.
Molecular Cell 48, Dec. 28, 2012, pp. 900-913.
Transcription 2010, Jul.-Aug.; 1(1): pp. 17-21.
PLOS One, vol. 6, Issue 2, e17057, Feb. 1, 2011.
Front Physiol. 2018; 9: Article 135.
Diabetes, vol. 66, Oct. 2017, pp. 1159-1171.
Annals of Clinical & Laboratory Science, vol. 44., No. 4, 2014, pp. 410-418.
Hepatology, vol. 68, No. 5, 2018, pp. 1786-1803.
Experimental & Molecular Medicine (2019) 51:107, pp. 1-11.
Aging, May 2016, vol. 8, No. 5, pp. 1064-1078.
Cell Reports, vol. 18, Issue 8, Feb. 21, 2017, pp. 1858-1868.
Cell Reports, vol. 13, Issue 3, Oct. 20, 2015, pp. 479-488.
Cell vol. 151, Issue 6, Dec. 7, 2012, pp. 1185-1199.
Cell Cycle 10:18, Sep. 15, 2011, pp. 3153-3158.
Carcinogenesis, 34(7), Jul. 2013, pp. 1476-86.
Circulation Research, vol. 124, No. 10, 2019, pp. 1448-1461.
The Journal of Biological Chemistry 2013, 288 (41), pp. 29252-29259.
Molecular Medicine Reports 17: 2018; pp. 4035-4042.
Biochemical and Biophysical Research Communications, vol. 466, Issue 3, Oct. 23, 2015, pp. 319-326.
Sci Rep 7, Article No. 11877 (2017).
Int. J. Mol. Sci. 2019, 20(5), 1153, pp. 1-10.
European Journal of Pharmacology, vol. 859, Sep. 15, 2019.
Experimental Cell Research vol. 330, Issue 1, Jan. 1, 2015, pp. 81-90.
Invest. Ophthalmo. Vis. Sci. 2013; 54(15): 6078.
Nature 560, (2018) pp. 661-665.
Gene Dev., Mar. 1, 2018, 32(5-6), pp. 373-388.

* cited by examiner

*Primary Examiner* — Joseph R Kosack
(74) *Attorney, Agent, or Firm* — Graeser Associates International, Inc.; Dvorah Graeser

(57) ABSTRACT

A SIRT6 activating molecule as shown in Tables 1-3 or a compound according to a pharmacophore as described herein.

8 Claims, 8 Drawing Sheets

| Feature # | Distance | | | |
|---|---|---|---|---|
| | 2 | 3 | 4 | 5 |
| 1 | 7.470 | 6.179 | 6.027 | 5.786 |
| 2 | | 6.464 | 10.967 | 2.756 |
| 3 | | | 5.700 | 3.855 |
| 4 | | | | 8.516 |

| Distance | | | | | |
|---|---|---|---|---|---|
| Feature # | 2 | 3 | 4 | 5 |
| 1 | 4.126 | 11.726 | 11.726 | 9.271 |
| 2 | | 10.059 | 10.059 | 6.663 |
| 3 | | | - | 4.290 |
| 4 | | | | 4.290 |

| Distance | | | | | |
|---|---|---|---|---|---|
| Feature # | 2 | 3 | 4 | 5 |
| 1 | 4.126 | 4.947 | 11.726 | 10.209 |
| 2 | | 4.839 | 10.059 | 9.266 |
| 3 | | | 7.008 | 5.385 |
| 4 | | | | 4.428 |

MOLECULES, COMPOSITIONS AND METHODS FOR MODULATION OF SIRT6

FIELD OF THE INVENTION

The present invention relates to novel molecules and compositions containing same for modulation of SIRT6, and methods of preparation and administration thereof.

BACKGROUND OF THE INVENTION

Sir2 family of enzymes, namely sirtuins, consists of seven mammalian enzymes (SIRT1 to SIRT7) that share a conserved core catalytic domain, but differ in tissue specificity, subcellular localization, enzymatic activity and targets. The sirtuins are NAD+-dependent enzymes that regulate a large number of diverse cellular pathways. Among the sirtuins, SIRT6, a chromatin-associated enzyme with deacetylase and long-chain deacylase activities, is considered to have a leading role in regulating genomic stability, cellular metabolism, stress response, and aging. SIRT6-deficient mice display shortened lifespan and acute degenerative and metabolic defects similar to premature aging pathologies, including loss of subcutaneous fat, lordokyphosis, colitis and severe lymphopenia. Additionally, transgenic mice overexpressing SIRT6 have a significantly longer life span than wild-type control mice, further supporting that SIRT6 is central in regulating aging processes. Furthermore, SIRT6 regulates glucose homeostasis and fat metabolism and suppresses obesity, fatty liver, glucose intolerance, inflammation, cardiac hypertrophy and cellular senescence.

SUMMARY OF THE INVENTION

Accumulating data indicate that SIRT6 is the sirtuin with special relevance for regulating aging processes and metabolism. SIRT6 is involved in several DNA repair pathways and associates specifically with telomeres. Inactivation of SIRT6 leads to hypersensitivity to DNA damage, loss of telomere protection and genomic instability. Thus, SIRT6 protects tissues from telomere dysfunction, promotes genome stability and resistance to DNA damage and oxidative stress, the principal defects associated with age-related diseases and cancer. As genomic instability and altered metabolism are hallmarks of many cancers, SIRT6 was shown to act as tumor suppressor also by controlling cancer metabolism (inhibition of Warburg effect). Moreover, SIRT6 was found to be a major regulator of glucose homeostasis and fat metabolism. SIRT6 is a critical regulator of cholesterol homeostasis and involved in regulation of lipogenesis by repression of lipogenic transcription factors, SREBP1 and SREBP2. SIRT6 transgenic mice fed a high fat diet are protected against fat accumulation, elevated triglyceride and LDL cholesterol levels and impaired glucose tolerance. The involvement of SIRT6 in fat metabolism is further supported by the finding that liver specific SIRT6 deletion results in liver steatosis. In addition, overexpression of SIRT6 improves aspects of age-associated metabolic decline such as glucose intolerance. On the whole, SIRT6 is a key regulator of metabolic homeostasis, the imbalance of which eventually accelerates aging and senescence.

SIRT1 was originally thought to be the most important sirtuin involved in aging and other disease processes, a role which is now believed to also be held by SIRT6. However, it has recently been found that SIRT1 and SIRT6 may in fact have different roles in various disease processes, for example with regard to metabolic diseases. An article by Masri et al (Cell, 2014, vol 158, pages 659-672) illustrates a difference between SIRT1 and SIRT6 in controlling cellular metabolism. SIRT1 and SIRT6, manage important liver processes (lipid storage and energy usage) separately and distinctly from each other. In an interview, the authors claimed (http://news.uci.edu/press-releases/strict-genomic-partitioning-by-biological-clock-separates-key-metabolic-functions/) that these findings may contribute to the design of pharmacological strategies targeting SIRT1- or SIRT6-specific metabolic functions and pathologies. Thus, SIRT6 specific modulation would be of clear importance for treating various diseases.

The background art does not teach or suggest effective molecules, compositions containing same, or methods of preparation and use thereof, for the modulation of SIRT6.

According to at least some embodiments, there are provided effective molecules, compositions containing same, or methods of preparation and use thereof, which are believed to be useful for the modulation of SIRT6 (without wishing to be limited by single hypothesis in terms of other additional or different activities that these molecules may have). These molecules are presented below in Tables 1-3, in Example 1, which describes the assay used to test these molecules for SIRT6 activity. The molecules in Tables 1-3 all showed the ability to activate SIRT6.

According to at least some embodiments, the SIRT6 modulators may optionally be used to treat obesity or an obesity-related disease, or a fat-related metabolic disorder.

"Obesity" refers to a condition in which a subject has a body mass index of greater than or equal to 30. "Overweight" refers to a condition in which a subject has a body mass index of greater or equal to 25.0. The body mass index and other definitions are according to the "NIH Clinical Guidelines on the Identification and Evaluation, and Treatment of Overweight and Obesity in Adults" (1998). In particular, obesity can lead to type II diabetes in successive phases. Clinically, these phases can be characterized as normal glucose tolerance, impaired glucose tolerance, hyperinsulinemic diabetes, and hypoinsulinemic diabetes. Such a progressive impairment of glucose storage correlates with a rise in basal glycemia.

"Obesity-related disease" and "Fat-related metabolic disorder" include, but are not limited to, anorexia nervosa, wasting, AIDS-related weight loss, bulimia, cachexia, lipid disorders including hyperlipidemia and hyperuricemia, insulin resistance, noninsulin dependent diabetes mellitus (NIDDM, or Type II diabetes), insulin dependent diabetes mellitus (IDDM or Type I diabetes), diabetes-related complications including microangiopathic lesions, ocular lesions, retinopathy, neuropathy, and renal lesions, cardiovascular disease (including cardiac insufficiency, coronary insufficiency, and high blood pressure), atherosclerosis, atheromatous disease, stroke, hypertension, Syndrome X, gallbladder disease, osteoarthritis, sleep apnea, forms of cancer such as uterine, breast, colorectal, kidney, and gallbladder, high cholesterol levels, complications of pregnancy, menstrual irregularities, hirsutism, muscular dystrophy, infertility, a weight-related disorder (characterized by a subject being over or under weight, e.g., being within the top or bottom 25th percentile of body mass index) and increased surgical risk. In preferred embodiments, a treated or diagnosed subject is a mammal, preferably a human.

Fat-related metabolic disorders include disorders in which (i) increased fat storage, reduced fat mobilization, and/or reduced fat burning is desired, and (ii) other disorders in which reduced fat storage, increased fat mobilization and/or increased fat burning is desired. Examples of the first category of disorders include, e.g., anorexia nervosa, wasting, AIDS-related weight loss, bulimia, cachexia. Examples of the latter category include, e.g., obesity, cardiovascular disease, osteoarthritis. The classification of other disorders (e.g., infertility, increased surgical risk, pregnancy complications) may depend on the weight of the subject, e.g., whether the subject is over- or underweight. Overweight subjects can be treated, e.g., with an agent that increases SIRT6 activity, and underweight subject can be treated, e.g., with an agent that decreases SIRT6 activity.

Optionally, the above diseases may also be treatable by SIRT6 modulators in cases where the subject is not obese according to the definition of BMI (body mass index), which requires a BMI of at least 30 for obesity. Instead, the above diseases may also optionally be treatable by SIRT6 modulators in subjects in which body tissue composition, such as for example body fat percentage, results in one of the above diseases. Furthermore, SIRT6 modulators may also optionally be able to treat subjects suffering from sub-optimal body tissue composition, such as for example higher than desired body fat percentage. While the definition of higher than desired body fat percentage may vary, it may for example relate to a percentage in any integral amount starting at least at 20%, at least at 25%, at least at 30%, at least at 40%, at least at 45% and any amount in between.

SIRT6 modulators may also optionally be used to treat subjects suffering from sub-optimal body fat distribution, such as for example excess abdominal fat, which has been shown to lead to a higher risk of various diseases, including without limitation the above diseases. SIRT6 modulators may optionally be used to treat body fat distribution directly and/or one of the above diseases associated with obesity or fat-related metabolic disorders.

Sirt6 modulators may also optionally be used to treat metabolic diseases that are not necessarily related to fat or to obesity, and/or in which the subject is not obese or even overweight. For such diseases, metabolic disorders are defined as conditions, diseases, and disorders associated with glucose and/or lipid metabolism dysregulation, including but not limited to: type 2 diabetes, prediabetes, glucose intolerance, insulin insensitivity, hyperglycemia, hypoglycemia, gestational diabetes, drug-induced diabetes; overweight, obesity, high percent body fat and/or body composition and/or body fat location, dyslipidemia defined as abnormal levels of blood lipids such as cholesterol, triglycerides and free fatty acids; and non-alcoholic fatty liver disease (NAFLD) ranging from steatosis to steatohepatitis (NASH), advanced fibrosis and cirrhosis.

According to at least some embodiments, the SIRT6 modulators may optionally be used to treat diseases associated with aging and senescence, including but not limited to cardiovascular disease, neurodegenerative diseases, premature aging syndromes and aging. Optionally and preferably, these diseases are selected from the group described below (described according to various physiological systems for the sake of clarity only and without any intention of being limiting):

SKIN: Loss of subcutaneous fat, Decrease in Collagen elasticity, Xerosis, Senile Purpura, Pruritis, Pressure ulcers, Venous and Arterial ulcers, Skin cancer, Aging-related skin lesions such as Skin tags (Acrochordon) and Keratosis.

SKELETAL SYSTEM: Osteoporosis, Arthritis, Osteomalacia, Paget's disease

MUSCLES: Muscle wasting and/or atrophy, Muscle cramps, Myasthenia Gravis, Polymyalgia Rheumatica, Bursitis NERVOUS SYSTEM: Tremor, Parkinson's disease, Tardive Dyskinesia, Sleep Disorders, Brain tumors, Delirium, Various forms of Dementia including Alzheimer's disease.

SENSORY SYSTEM: Cataract, Glaucoma, Diabetic Retinopathy, Age-Related Macular Degeneration (AMD), Hearing loss, Tinnitus, Otosclerosis, Meniere's disease, Olfactory distortion.

CARDIOVASCULAR SYSTEM: Arteriosclerosis (lessened elasticity of artery walls), Atherosclerosis (fatty deposits on inner walls of arteries), Hypertension, Postural Hypotension, Acute Coronary Syndrome, Angina Pectoris, Myocardial Infraction, Congestive Heart Failure (CHF), Heart Valve disease, Cardiac Arrhythmias and Conduction disorders, Transient Ischemic Attack (mini-stroke), Cerebrovascular accident (Stroke), Aneurysm, Arterial Occlusion, Age-dependent increase of thromboembolic events RESPIRATORY SYSTEM: Chronic Obstructive Pulmonary disease (COPD), Chronic Bronchitis, Emphysema, Pulmonary Tuberculosis (TB), Pneumonia, Lung cancer.

GASTROINTESTINAL SYSTEM: Age-Related Disorders of the Mouth, Esophagus, Stomach, Small Intestine, Large Intestine, Pancreas, Liver and Gallbladder including Xerostomia (dry mouth), Dysphagia (difficulty swallowing), Periodontal disease, Oral cancer, Gastroesophageal Reflux disease, Hiatal Hernia, Cancer of the Esophagus, Gastritis (inflammation of the stomach), Gastric Ulcer, Cancer of the Stomach, Cancer of the Colon and Rectum, Hemorrhoids, Cancer of the Pancreas, Cirrhosis, Gallstones (Cholelithiasis).

ENDOCRINE SYSTEM: Pancreatitis, Pancreatic cancer

URINARY SYSTEM: Urinary Tract Infections (UTIs), Cystitis (lower urinary tract infection), Pyelonephritis (upper urinary tract infection), Acute Glomerulonephritis, Benign Prostatic Hyperplasia (BPH), Nephrolithiasis (kidney stone disease), Cancer of the Bladder, Urinary Incontinence, Renal Failure.

REPRODUCTIVE SYSTEM: 1. Female: Atrophic Vaginitis, Pelvic Organ Prolapse, Cancer of the cervix, uterus, ovary or breast. 2. Male: Cancer of the Prostate According to at least some embodiments, the SIRT6 modulators may optionally be used to treat cancer, optionally selected from the group consisting of but not limited to breast cancer, cervical cancer, ovary cancer, endometrial cancer, melanoma, uveal melanoma, bladder cancer, lung cancer, pancreatic cancer, colorectal cancer, prostate cancer, leukemia, acute lymphocytic leukemia, chronic lymphocytic leukemia, B-cell lymphoma, Burkitt's lymphoma, multiple myeloma, Non-Hodgkin's lymphoma, myeloid leukemia, acute myelogenous leukemia (AML), chronic myelogenous leukemia, thyroid cancer, thyroid follicular cancer, myelodysplastic syndrome (MDS), fibrosarcomas and rhabdomyosarcomas, teratocarcinoma, neuroblastoma, glioma, glioblastoma, benign tumor of the skin, keratoacanthomas, renal cancer, anaplastic large-cell lymphoma, esophageal cancer, follicular dendritic cell carcinoma, seminal vesicle tumor, epidermal carcinoma, spleen cancer, bladder cancer, head and neck cancer, stomach cancer, liver cancer, bone cancer, brain cancer, cancer of the retina, biliary cancer, small bowel cancer, salivary gland cancer, cancer of uterus, cancer of testicles, cancer of connective tissue, myelodysplasia, Waldenström's macroglobinaemia, nasopharyngeal, neuroendocrine cancer, mesothelioma, angiosarcoma, Kaposi's sarcoma, carcinoid, fallopian tube cancer, peritoneal cancer, papillary serous mullerian cancer, malignant ascites, gastrointestinal stromal tumor (GIST), Li-Fraumeni syndrome, and Von Hippel-Lindau syndrome (VHL).

According to at least some embodiments, the SIRT6 modulators may optionally be used to treat cancer, optionally selected from the group consisting of but not limited to breast cancer, cervical cancer, ovary cancer, endometrial cancer, melanoma, uveal melanoma, bladder cancer, lung cancer, pancreatic cancer, colorectal cancer, prostate cancer, leukemia, acute lymphocytic leukemia, chronic lymphocytic leukemia, B-cell lymphoma, Burkitt's lymphoma, multiple myeloma, Non-Hodgkin's lymphoma, myeloid leukemia, acute myelogenous leukemia (AML), chronic myelogenous leukemia, thyroid cancer, thyroid follicular cancer, myelodysplastic syndrome (MDS), fibrosarcomas and rhabdomyosarcomas, teratocarcinoma, neuroblastoma, glioma, glioblastoma, benign tumor of the skin, keratoacanthomas, renal cancer, anaplastic large-cell lymphoma, esophageal cancer, follicular dendritic cell carcinoma, seminal vesicle tumor, epidermal carcinoma, spleen cancer, bladder cancer, head and neck cancer, stomach cancer, liver cancer, bone cancer, brain cancer, cancer of the retina, biliary cancer, small bowel cancer, salivary gland cancer, cancer of uterus, cancer of testicles, cancer of connective tissue, myelodysplasia, Waldenstrom's macroglobinaemia, nasopharyngeal, neuroendocrine cancer, mesothelioma, angiosarcoma, Kaposi's sarcoma, carcinoid, fallopian tube cancer, peritoneal cancer, papillary serous mullerian cancer, malignant ascites, gastrointestinal stromal tumor (GIST), Li-Fraumeni syndrome, and Von Hippel-Lindau syndrome (VHL).

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

DESCRIPTION OF THE PREFERRED EMBODIMENTS

Figure 1:
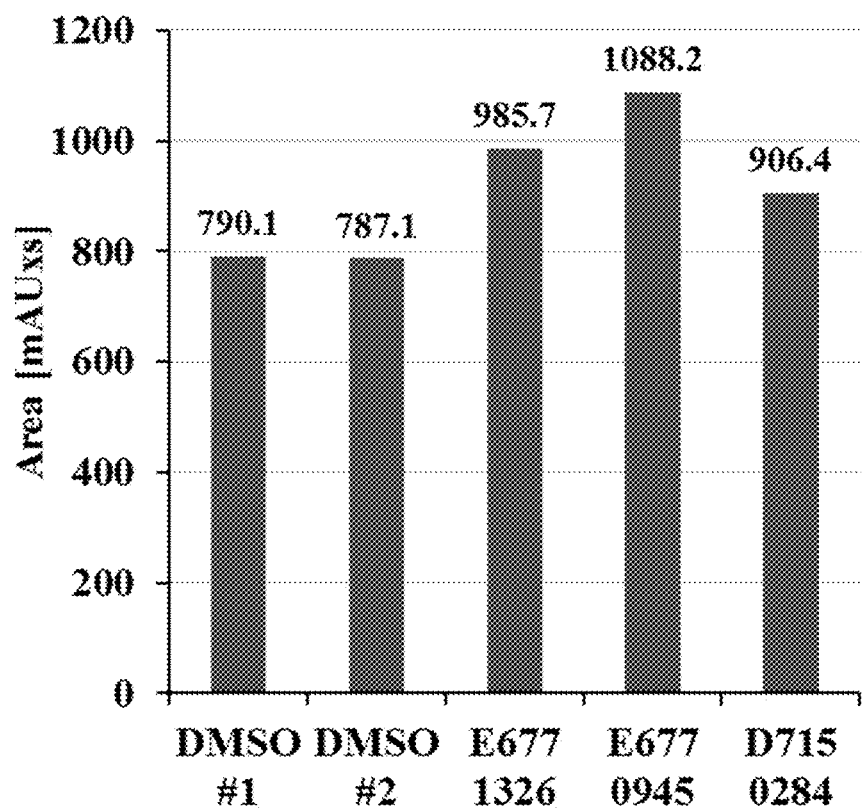
FIG. 1 shows the area under the peak corresponding to the amount of deacylated product after incubation with the compounds, in comparison to the DMSO control.

Example 1—Description of SIRT6 Activating Molecules and Demonstration of their Activity Tables 1-3 below show some exemplary SIRT6 activating molecules, as well as their activity levels in a particular assay, as described below. Without wishing to be limited in any way, it is noted that the molecules in Table 1 showed greater activity in this particular assay.

Expression and Purification of SIRT6 Protein

Human recombinant SIRT6 (sequence identifier: CAG33481.1; GI:4814651) was expressed in large scale in *Escherichia coli* strain BL21 as a six-histidine-tagged protein, after transformation of the expression plasmid pET28-SIRT6. The SIRT6 enzyme was purified from the bacteria culture broth in a two-step strategy. The first purification step was carried out by cation exchange chromatography on a HiTrap CM-Sepharose column (GE Healthcare) using an FPLC system. The second purification step was performed by immobilized metal ion affinity chromatography (IMAC) using a cobalt affinity column (Clontech).

Method of Assay

The enzymatic activity assay is carried out in 96 or 384-well microplates using the purified recombinant SIRT6 and a fluorophore-labeled peptide substrate: 7-amino-4-methylcoumarin (AMC) that is quenched through conjugation to the C-terminal end of a Lysin-myristoylated histone H3 peptide. The activity assay procedure requires two steps, both performed in the same microplate. In the first step, the substrate is incubated with the purified SIRT6 protein along with the co-substrate nicotinamide adenine dinucleotide (NAD+). Upon de-myristoylation, the liberated ε-amino group of the lysine becomes a trypsin substrate. Treatment with trypsin in the second step releases the fluorophore resulting in an increase in fluorescence. Fluorescence intensity is measured using a fluorescent plate reader (excitation and emission at 370 nm and 450 nm, respectively). The fluorescence signal is directly proportional to SIRT6 enzymatic activity.

High Throughput Screening

In the primary screening, compounds from a library (ChemDiv Inc.) were tested at a single concentration of 20 micromolar for their potential to modulate SIRT6 enzymatic activity. The assay was carried out in 384-well black well plates and all liquid handling was done using a robotic liquid handler. Purified recombinant SIRT6 (1 micromolar) was pre-incubated with each compound (or DMSO in control wells) for 15 minutes at room temperature. The first stage of the assay was initiated by adding a 'substrate solution' containing the myristoylated histone H3 peptide and NAD+ (for final concentrations of 25 micromolar and 20 micromolar, respectively). After one hour incubation at 37° C., a Trypsin solution (6 mg/mL) was added for 30 minutes at room temperature. Fluorescence intensity was measured using a fluorescent plate reader (Tecan) with excitation at 370 nm and emission at 450 nm. The effect of each tested compound was evaluated by the change in the fluorescence intensity compared to control wells. The compounds that demonstrated higher fluorescence intensity in comparison with control wells were considered as primary "hits". 'Activator' activity is defined as the percentage of signal increase relative to the average signal in control wells. To validate the primary screening results, each of the primary "hits" was re-tested, first at concentration of 20 micromolar in duplicates and later at a serial dilution ranging from 100 to 0.2 micromolar in triplicates.

Results of Assay—

The results of the assay are given below in Tables 1-3. For each table, column 1 gives an internal identifier; column 2 gives the CAS number for the molecule while column 3 shows its ChemDiv ID; column 4 gives the molecular structure; and column 5 shows percent activity of the molecule in the above assay, at two concentrations: 20 micromolar (left) and 100 micromolar (right). It should be noted that molecule "c" (third row of Table 1) is a specific stereoisomer as the other stereoisomer was not shown to be active in this assay (data on the other stereoisomer not shown, which has the CAS number 768382-41-8, as no specific CAS number has been assigned to the current stereoisomer in the table; this CAS number only represents the other stereoisomer that is not shown).
TABLE 1
| # | CAS number | ChemDiv ID | Structure | % activity 20 uM | Max. conc. 100 uM |
|---|---|---|---|---|---|
| A | 931369-52-7 | E677-0945 | 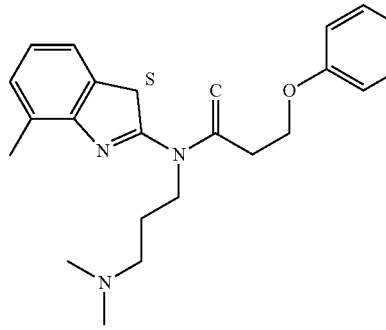 | 263 | 255 |
| B | 931312-00-4 | E677-1326 | 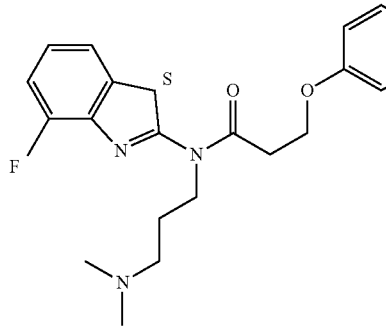 | 287 | 252 |
| C | stereoisomer of molecule 768382-41-8 | D715-0284 | 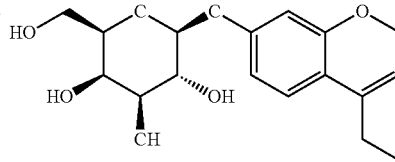 | 70 | 195 |
TABLE 2
| # | CAS number | ChemDiv ID | Structure | % activity 20 uM | 100 uM |
|---|---|---|---|---|---|
| 1 | 332173-46-3 | 2803-0068 | 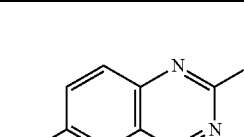 | 88 | 428 |

TABLE 2-continued

| # | CAS number | ChemDiv ID | Structure | % activity 20 uM | % activity 100 uM |
|---|---|---|---|---|---|
| 2 | 351469-45-9 | 3389-1644 | 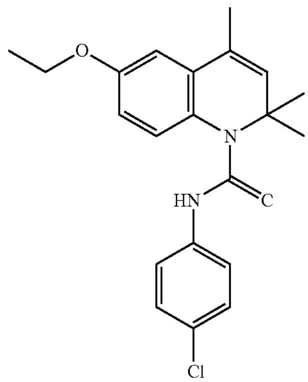 [SMILES: C=C(Nc1ccc(Cl)cc1)N1c2ccc(OCC)cc2C(C)=CC1(C)C] | 29 | 46 |
| 3 | 443677-66-5 | 4285-2380 | 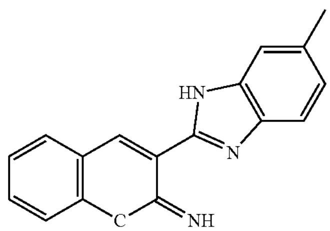 [SMILES: Cc1ccc2nc(C3=Cc4ccccc4CC3=N)[nH]c2c1] | 25 | 33 |
| 4 | 328286-54-0 | 4477-0762 | 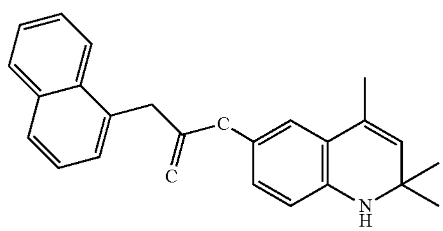 [SMILES: C=C(Cc1ccc2c(c1)C(C)=CC(C)(C)N2)Cc1cccc2ccccc12] | 29 | 56 |
| 5 | 375359-94-7 | 4477-2607 | 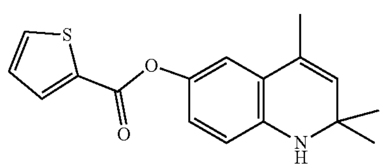 [SMILES: CC1=CC(C)(C)Nc2ccc(OC(=O)c3cccs3)cc21] | 39 | 54 |
| 6 | 353516-56-0 | 4896-3248 | 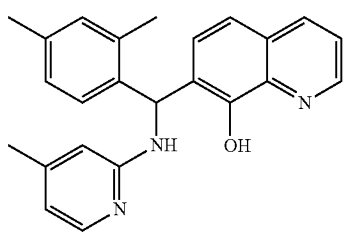 [SMILES: Cc1ccnc(NC(c2ccc(C)cc2C)c2ccc3cccnc3c2O)c1] | 30 | 28 |
| 7 | 797029-49-3 | 6843-3168 | 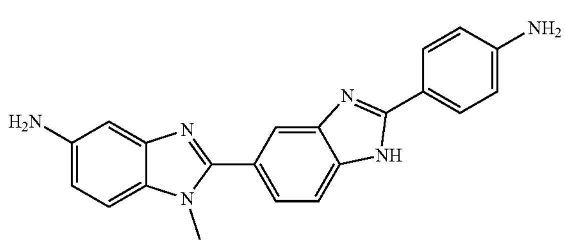 [SMILES: Cn1c(-c2ccc3[nH]c(-c4ccc(N)cc4)nc3c2)nc2cc(N)ccc21] | 118 | 162 |

TABLE 2-continued

| # | CAS number | ChemDiv ID | Structure | % activity | |
|---|---|---|---|---|---|
| | | | | 20 uM | 100 uM |
| 8 | 339156-78-4 | 8001-8196 | 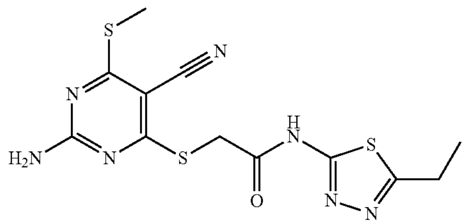 [SMILES: CCc1nnc(NC(=O)CSc2nc(N)nc(SC)c2C#N)s1] | 25 | 25 |
| 9 | 99254-31-6 | 8008-0525 | 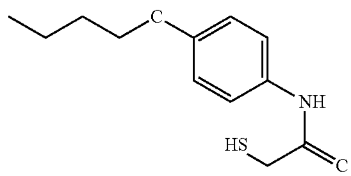 [SMILES: C=C(CS)Nc1ccc(CCCCC)cc1] | 22 | 48 |
| 10 | 300588-35-6 | 8008-8279 | 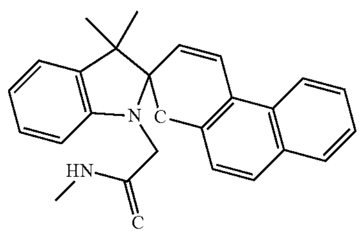 [SMILES: C=C(CN1c2ccccc2C(C)(C)C12C=Cc1c(ccc3ccccc13)C2)NC] | 25 | 27 |
| 11 | 70598-96-8 | 8010-0818 | 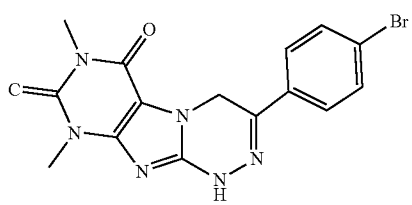 [SMILES: C=C1N(C)C(=O)c2c(nc3n2CC(c2ccc(Br)cc2)=NN3)N1C] | 41 | 99 |
| 12 | 442642-14-0 | 8012-5593 | 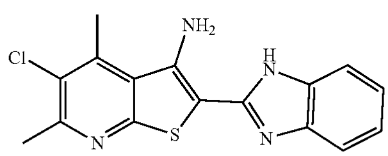 [SMILES: Cc1nc2sc(-c3nc4ccccc4[nH]3)c(N)c2c(C)c1Cl] | 36 | 59 |
| 13 | 515875-10-2 | 8013-3307 | 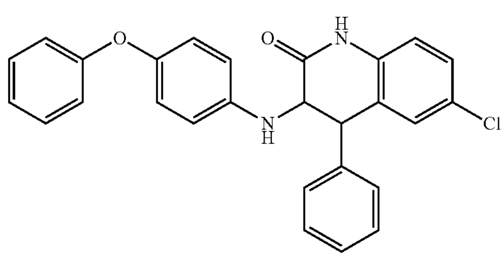 [SMILES: O=C1Nc2ccc(Cl)cc2C(c2ccccc2)C1Nc1ccc(Oc2ccccc2)cc1] | 24 | 86 |
| 14 | 24386-17-2 | 8014-9229 | 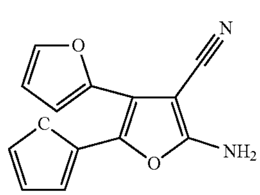 [SMILES: N#Cc1c(N)oc(C2=CC=CC2)c1-c1ccco1] | 28 | 48 |

TABLE 2-continued

| # | CAS number | ChemDiv ID | Structure | % activity | |
|---|---|---|---|---|---|
| | | | | 20 uM | 100 uM |
| 15 | 290299-89-7 | 8018-3339 | 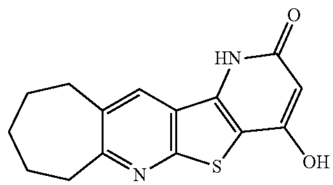 [SMILES: O=c1cc(O)c2sc3nc4c(cc3c2[nH]1)CCCCC4] | 37 | 75 |
| 16 | 128294-19-9 | 8018-4551 | 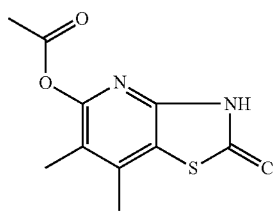 [SMILES: C=C1Nc2nc(OC(C)=O)c(C)c(C)c2S1] | 40 | 197 |
| 17 | 879058-43-2 | 8018-6508 | 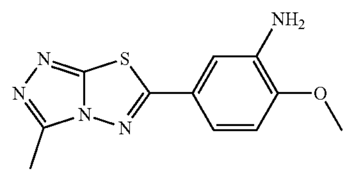 [SMILES: COc1ccc(-c2nn3c(C)nnc3s2)cc1N] | 21 | 18 |
| 18 | 879765-85-2 | 8020-1200 | 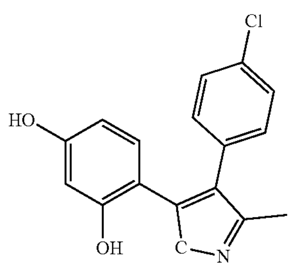 [SMILES: CC1=NCC(c2ccc(O)cc2O)=C1c1ccc(Cl)cc1] | 53 | 94 |
| 19 | 1005160-87-1 | C142-0098 | 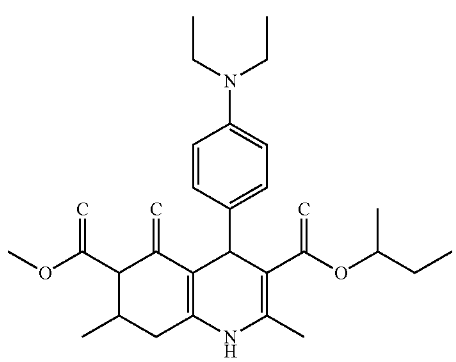 [SMILES: C=C(OC(C)CC)C1=C(C)NC2=C(C(=C)C(C(=C)OC)C(C)C2)C1c1ccc(N(CC)CC)cc1] | 37 | 61 |
| 20 | 1031990-46-1 | C201-1744 | 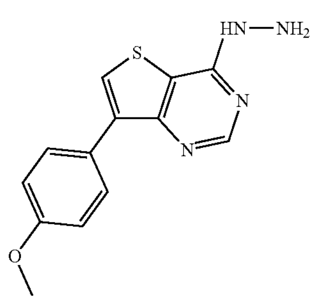 [SMILES: COc1ccc(-c2csc3c(NN)ncnc23)cc1] | 78 | 22 |

TABLE 2-continued

| # | CAS number | ChemDiv ID | Structure | % activity 20 uM | 100 uM |
|---|---|---|---|---|---|
| 21 | 901014-49-1 | C381-0232 | 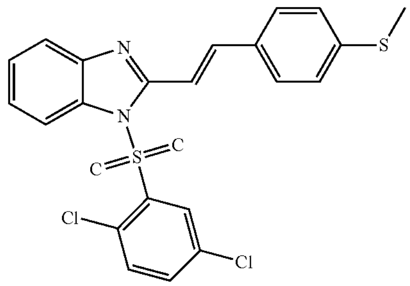 [SMILES: C=S(=C)(c1cc(Cl)ccc1Cl)n1c(/C=C/c2ccc(SC)cc2)nc2ccccc21] | 38 | 36 |
| 22 | 902559-22-2 | C535-0969 | 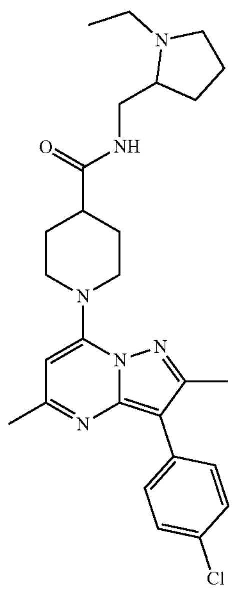 [SMILES: CCN1CCCC1CNC(=O)C1CCN(c2cc(C)nc3c(-c4ccc(Cl)cc4)c(C)nn23)CC1] | 32 | 29 |
| 23 | 1017523-49-7 | D506-0127 | 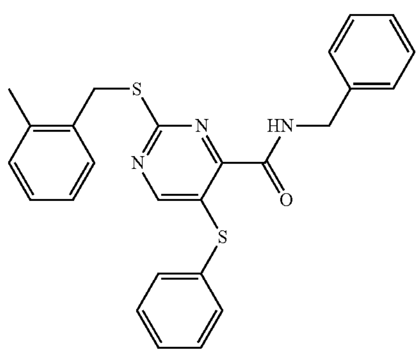 [SMILES: Cc1ccccc1CSc1ncc(Sc2ccccc2)c(C(=O)NCc2ccccc2)n1] | 55 | 65 |

TABLE 2-continued

| | | ChemDiv | | % activity | |
|---|---|---|---|---|---|
| # | CAS number | ID | Structure | 20 uM | 100 uM |
| 24 | 1293946-11-8 | D549-0050 | | 77 | 47 |
| 25 | 1358629-50-1 | D577-0290 | | 26 | 22 |
| 26 | 1474056-79-5 | D715-0292 | | 21 | 56 |
| 27 | 950279-39-7 | E146-0990 | | 59 | 137 |

TABLE 2-continued
| # | CAS number | ChemDiv ID | Structure | % activity 20 uM | 100 uM |
|---|---|---|---|---|---|
| 28 | 938025-58-2 | F025-0094 | 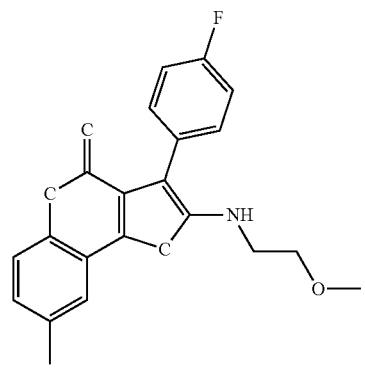 [SMILES: C=C1Cc2ccc(C)cc2C2=C1C(c1ccc(F)cc1)=C(NCCOC)C2] | 134 | 246 |
| 29 | 938026-06-3 | F025-0098 | 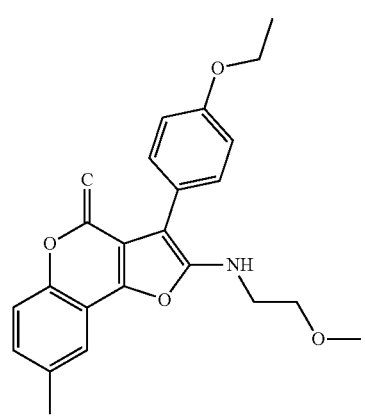 [SMILES: C=C1Oc2ccc(C)cc2-c2oc(NCCOC)c(-c3ccc(OCC)cc3)c21] | 82 | 226 |
| 30 | 938025-40-2 | F025-0102 | 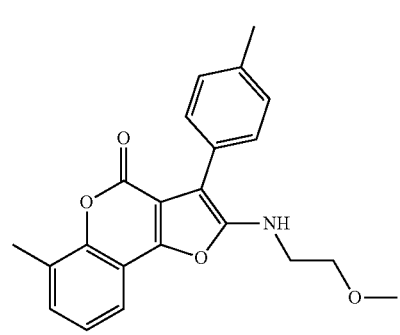 | 149 | 111 |
| 31 | 932969-43-2 | F498-0132 | 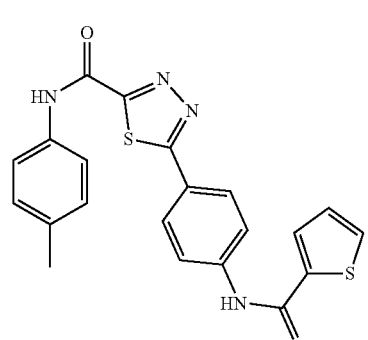 | 29 | 16 |

TABLE 2-continued

| # | CAS number | ChemDiv ID | Structure | % activity 20 uM | 100 uM |
|---|---|---|---|---|---|
| 32 | 1040683-42-8 | G744-0071 | 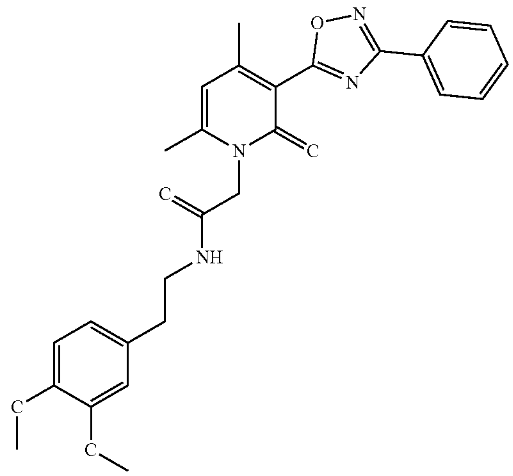 [SMILES: C=C(CN1C(=C)C(c2nc(-c3ccccc3)no2)=C(C)C=C1C)NCCc1ccc(CC)c(CC)c1] | 101 | 73 |
| 33 | 1040572-56-4 | G744-0080 | 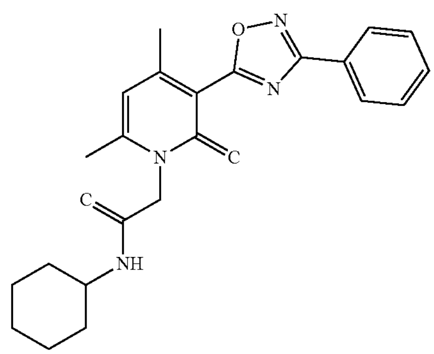 [SMILES: C=C(CN1C(=C)C(c2nc(-c3ccccc3)no2)=C(C)C=C1C)NC1CCCCC1] | 53 | 221 |
| 34 | 1206085-08-6 | G755-0539 | 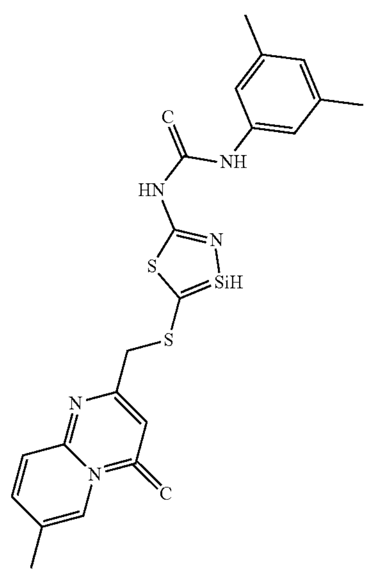 | 34 | 87 |
| 35 | 933226-39-2 | G891-0058 | 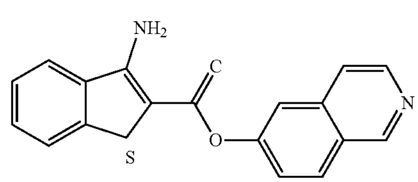 | 154 | 324 |

TABLE 2-continued

| # | CAS number | ChemDiv ID | Structure | % activity 20 uM | 100 uM |
|---|---|---|---|---|---|
| 36 | 1446199-09-2 | H024-0026 | 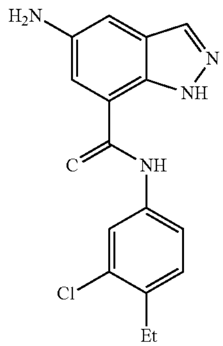 [SMILES: C=C(Nc1ccc(CC)c(Cl)c1)c1cc(N)cc2cn[nH]c12] | 45 | 56 |
| 37 | 422272-66-0 | K232-1782 | 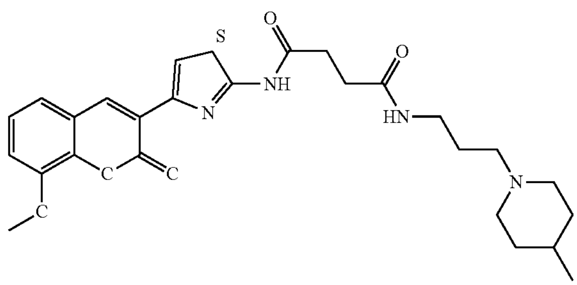 | 42 | 35 |
| 38 | 899707-19-8 | K906-5001 | 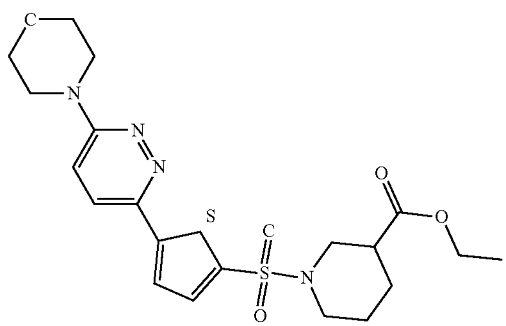 | 52 | 52 |
| 39 | 434925-30-1 | K937-0320 | 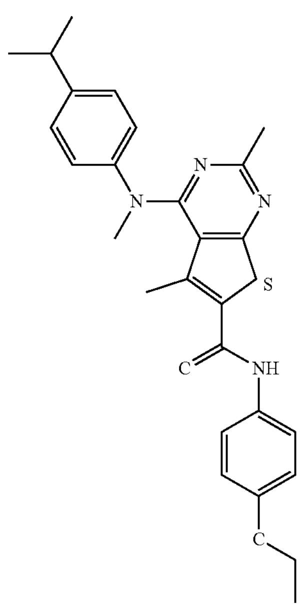 | 32 | 54 |

TABLE 2-continued

| # | CAS number | ChemDiv ID | Structure | % activity 20 uM | 100 uM |
|---|---|---|---|---|---|
| 40 | 1115352-35-6 | L036-0162 | 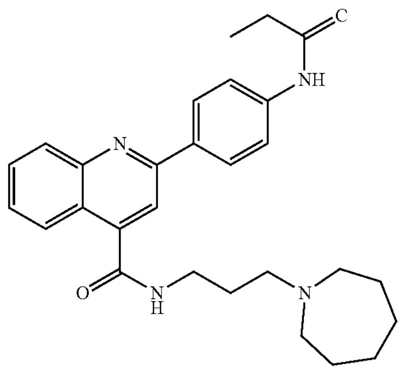 [SMILES: C=C(CC)Nc1ccc(-c2cc(C(=O)NCCCN3CCCCCC3)c3ccccc3n2)cc1] | 62 | 92 |
| 41 | 1115421-77-6 | L036-0163 | 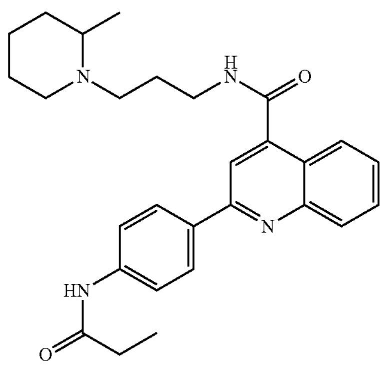 [SMILES: CCC(=O)Nc1ccc(-c2cc(C(=O)NCCCN3CCCCC3C)c3ccccc3n2)cc1] | 40 | 110 |
| 42 | 1115317-33-3 | L036-0174 | 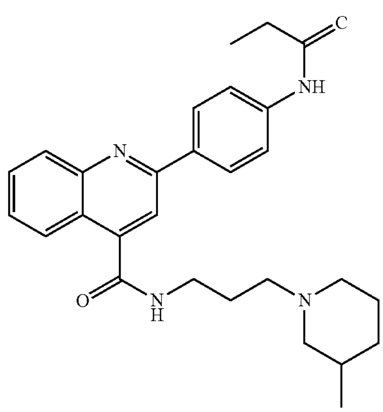 [SMILES: C=C(CC)Nc1ccc(-c2cc(C(=O)NCCCN3CCCC(C)C3)c3ccccc3n2)cc1] | 61 | 87 |
| 43 | 1115317-58-2 | L036-2289 | 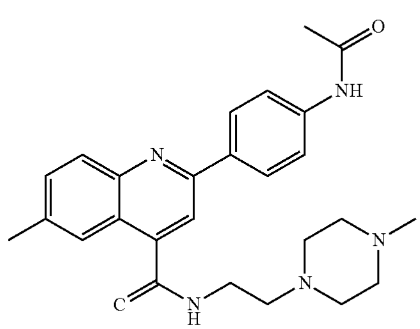 | 96 | 119 |

TABLE 2-continued

| # | CAS number | ChemDiv ID | Structure | % activity 20 uM | 100 uM |
|---|---|---|---|---|---|
| 44 | 1115370-79-0 | L103-0652 | 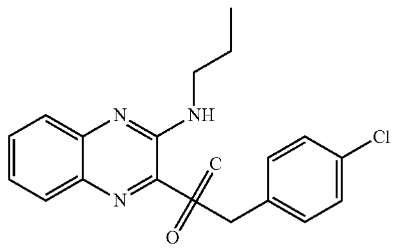 | 34 | 42 |
| 45 | 1115370-86-9 | L103-0696 | 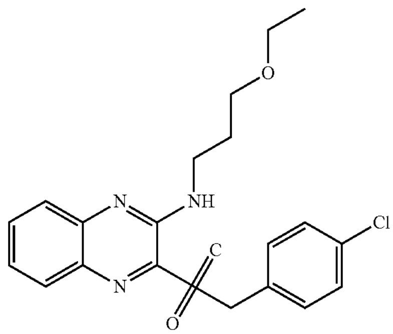 | 91 | 159 |
| 46 | 1112327-81-7 | M049-1557 | 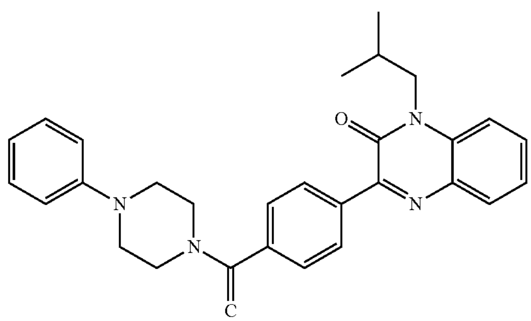 [SMILES: C=C(c1ccc(-c2nc3ccccc3n(CC(C)C)c2=O)cc1)N1CCN(c2ccccc2)CC1] | 51 | 56 |
| 47 | 1340850-02-3 | M715-0111 | 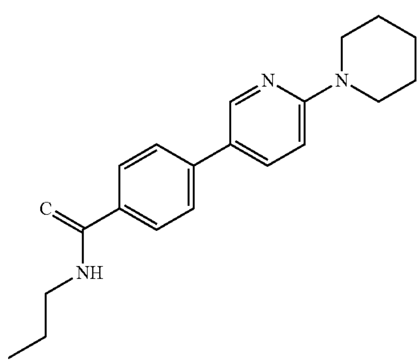 [SMILES: C=C(NCCC)c1ccc(-c2ccc(N3CCCCC3)nc2)cc1] | 63 | 50 |
| 48 | 1340765-63-0 | M715-0112 | 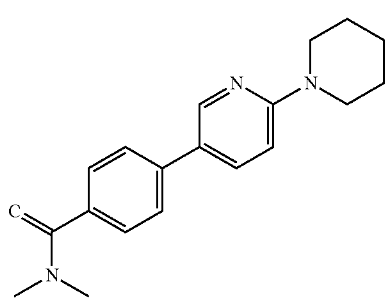 [SMILES: C=C(c1ccc(-c2ccc(N3CCCCC3)nc2)cc1)N(C)C] | 40 | 54 |

TABLE 2-continued

| # | CAS number | ChemDiv ID | Structure | % activity | |
|---|---|---|---|---|---|
| | | | | 20 uM | 100 uM |
| 49 | 1341007-09-7 | M715-0156 | 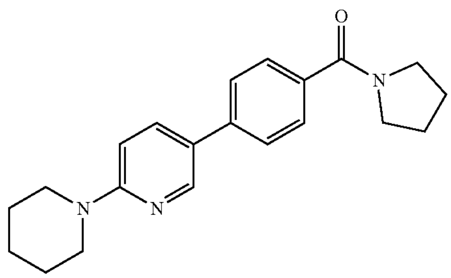 [SMILES: O=C(c1ccc(-c2ccc(N3CCCCC3)nc2)cc1)N1CCCC1] | 93 | 75 |
| 50 | 1358902-84-7 | M723-0069 | 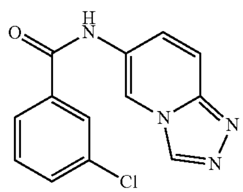 [SMILES: O=C(Nc1ccc2nncn2c1)c1cccc(Cl)c1] | 30 | 51 |
| 51 | 1243005-49-3 | M723-1403 | 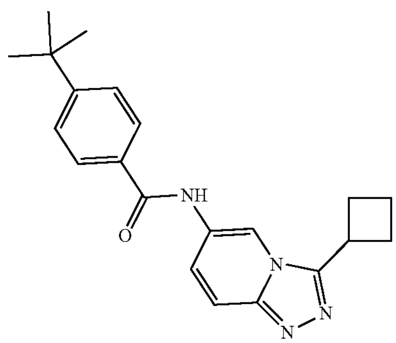 [SMILES: CC(C)(C)c1ccc(C(=O)Nc2ccc3nnc(C4CCC4)n3c2)cc1] | 23 | 87 |
| 52 | 1358277-15-2 | M723-1459 | 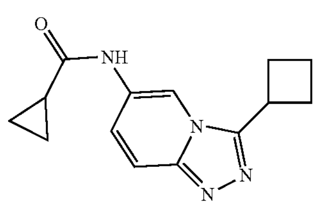 [SMILES: O=C(Nc1ccc2nnc(C3CCC3)n2c1)C1CC1] | 69 | 142 |
| 53 | 1091996-67-6 | M830-6517 | 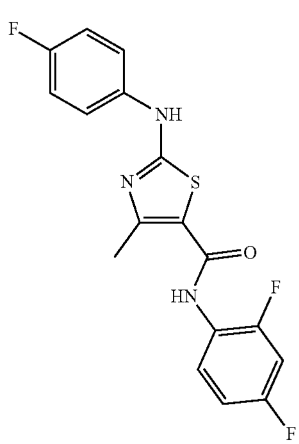 [SMILES: Cc1nc(Nc2ccc(F)cc2)sc1C(=O)Nc1ccc(F)cc1F] | 36 | 22 |

TABLE 2-continued

| # | CAS number | ChemDiv ID | Structure | % activity 20 uM | 100 uM |
|---|---|---|---|---|---|
| 54 | 1358236-69-7 | M830-6572 | 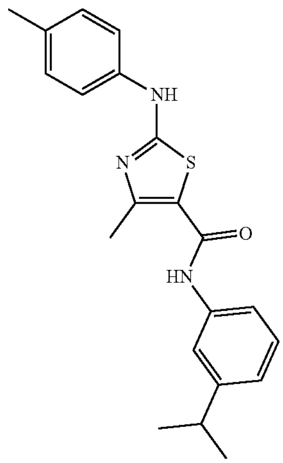 [SMILES: Cc1ccc(Nc2nc(C)c(C(=O)Nc3cccc(C(C)C)c3)s2)cc1] | 31 | 11 |
| 55 | 1358351-15-1 | P613-0273 | 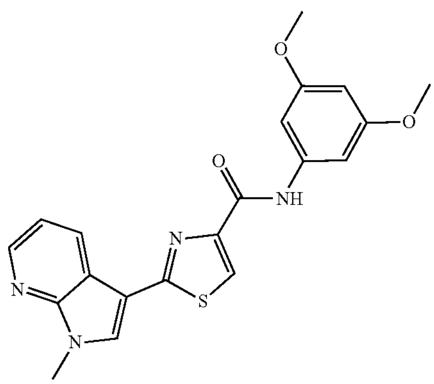 [SMILES: COc1cc(NC(=O)c2csc(-c3cn(C)c4ncccc34)n2)cc(OC)c1] | 31 | 37 |
| 56 | 1357727-05-9 | P933-1294 | 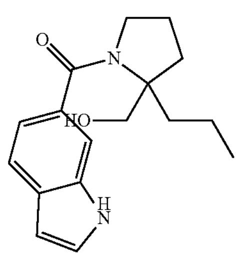 [SMILES: CCCC1(CO)CCCN1C(=O)c1ccc2cc[nH]c2c1] | 30 | 53 |
| 57 | 1340696-21-0 | P950-0537 | 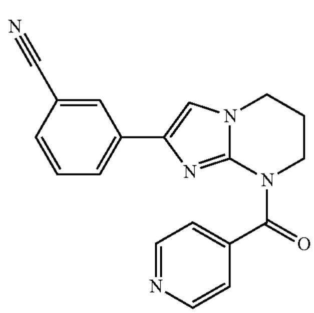 [SMILES: N#Cc1cccc(-c2cn3c(n2)N(C(=O)c2ccncc2)CCC3)c1] | 37 | 45 |

TABLE 2-continued

| # | CAS number | ChemDiv ID | Structure | % activity 20 uM | % activity 100 uM |
|---|---|---|---|---|---|
| 58 | 1775562-29-2 | S051-0094 | 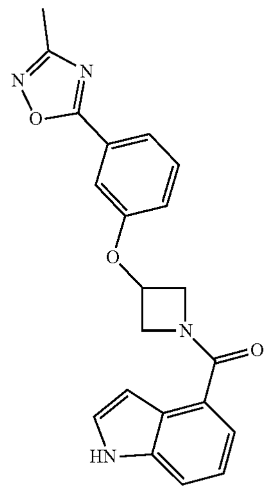 [SMILES: Cc1noc(-c2cccc(OC3CN(C(=O)c4cccc5[nH]ccc45)C3)c2)n1] | 38 | 47 |
| 59 | 1203182-84-6 | V004-5575 | 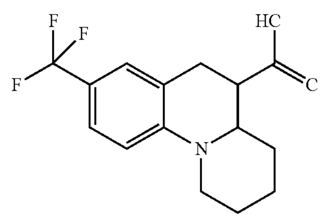 [SMILES: C=C(C)C1Cc2cc(C(F)(F)F)ccc2N2CCCCC12] | 89 | 175 |
| 60 | 1314203-44-5 | V030-4109 | 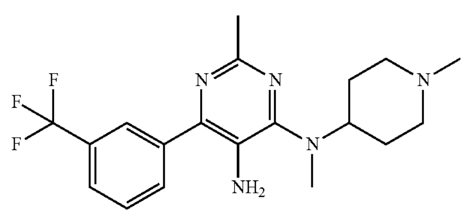 [SMILES: Cc1nc(-c2cccc(C(F)(F)F)c2)c(N)c(N(C)C2CCN(C)CC2)n1] | 52 | 255 |
| 61 | 1314211-30-7 | V030-4128 | 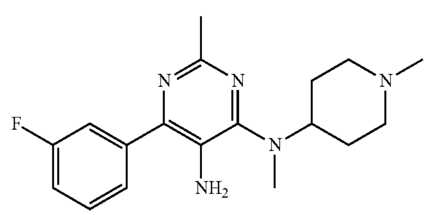 [SMILES: Cc1nc(-c2cccc(F)c2)c(N)c(N(C)C2CCN(C)CC2)n1] | 50 | 210 |
| 62 | 1173666-66-4 | Y040-3625 | 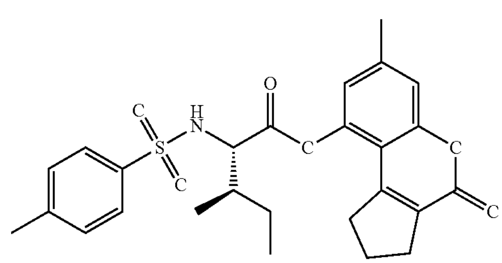 | 28 | 113 |

Table 3 shows an additional two structures with data at the 20 micromolar concentration only

| # | CAS number | ChemDiv ID | Structure | % activity (20 micromolar only) |
|---|---|---|---|---|
| 63 | 1357759-28-4 | M535-1335 | 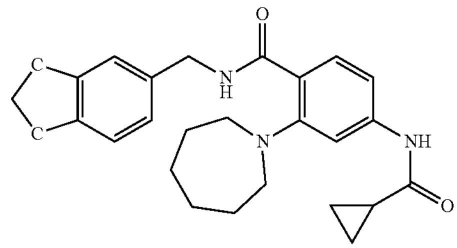 [SMILES: O=C(NCc1ccc2c(c1)CCC2)c1ccc(NC(=O)C2CC2)cc1N1CCCCCC1] | 38% |
| 64 | 902840-30-6 | E205-0117 | 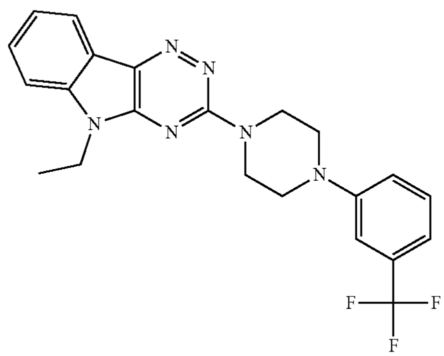 [SMILES: CCn1c2ccccc2c2nnc(N3CCN(c4cccc(C(F)(F)F)c4)CC3)nc21] | 85% |

Example 2—Compositions and Methods of Administration for SIRT6 Activating Molecules Pharmaceutical Compositions As used herein, the term "excipient" means the substances used to formulate active pharmaceutical ingredients (API) into pharmaceutical formulations; in a preferred embodiment, an excipient does not lower or interfere with the primary therapeutic effect of the API. Preferably, an excipient is therapeutically inert. The term "excipient" encompasses carriers, diluents, vehicles, solubilizers, stabilizers, bulking agents, acidic or basic pH-adjusting agents and preservatives. Excipients can also be those substances present in a formulation as an indirect or unintended result of the manufacturing process.

The term "sublingual administration" refers to the mode of administration of a medicament to the tissue under the tongue.

"Treating" or "treatment" of a disease includes: (1) preventing the disease, i.e., causing the clinical symptoms of the disease not to develop in a mammal that may be exposed to or predisposed to the disease but does not yet experience or display symptoms of the disease, (2) inhibiting the disease, i.e., arresting or reducing the development of the disease or its clinical symptoms, or (3) relieving the disease, i.e., causing regression of the disease or its clinical symptoms.

According to some embodiments, the composition may be administered in a form of a sublingual spray for quick systemic distribution, rapid therapeutic activity and ease of use.

In another embodiment, the sublingual spray formulations of the present invention can take various forms including, but not limited to, aqueous solutions, non-aqueous solutions and combinations thereof. Aqueous solutions include, for example, aqueous gels, aqueous suspensions, aqueous liposomal dispersions, aqueous emulsions, aqueous microemulsions and combinations thereof. Non-aqueous solutions include, for example, non-aqueous gels, non-aqueous suspensions, non-aqueous liposomal dispersions, non-aqueous emulsions, non-aqueous microemulsions and combinations thereof.

In another embodiment, the pH of the compositions may be maintained from about 3.0 to about 10.0. Compositions having a pH of less than about 3.0 or greater than about 10.0 can increase the risk of irritating the mucosal membranes in the sublingual region of a recipient. In another embodiment, the pH of the compositions is maintained from about 3.0 to about 7.0.

According to some embodiments, preservatives may be added to the present compositions. Suitable preservatives that can be used with the present compositions include benzyl alcohol, parabens, thimerosal, chlorobutanol and benzalkonium chloride and preferably benzalkonium chloride is used. In another embodiment, the preservative are present in a composition in a concentration of up to about 2% by weight.

In another embodiment, the compositions of the invention can be formulated so as to provide quick, sustained or delayed release of the active ingredient after administration to the patient by employing procedures known in the art. In another embodiment, the formulation may also comprise a muco-adherent to increase the residence time on the mucosa; including chitosan, polyvinyl pyrrolidone, or gelatin.

In another embodiment, the formulation may further comprise a moisturizing agent, such as propylene glycol, or polyethylene glycol. The formulation may further comprise an antioxidant, such as butylated hydroxyltoluene, ascorbic acid, alkyl gallates, or tocopherols. The formulation may further comprise an ionic or nonionic surfactant, such as sodium lauryl sulfate, or sorbitan esters.

In another embodiment, the formulation may further comprise a co-solvent. In another embodiment, the organic solvent is an alcohol. In another embodiment, the alcohol may comprise, but is not limited to, ethanol, propylene glycol, glycerol, polyethylene glycol and mixtures thereof. More preferably, the alcohol is ethanol. In another embodiment, the organic solvent is present in an amount of 0-90% w/w.

According to some demonstrative embodiments, the present invention may provide for compositions as described above which may be administered to the sublingual tissue under the tongue to a mammal to treat Fibromyalgia. In another embodiment, the formulation is administered as a spray. In another embodiment, the spray is administered directly to the sublingual mucosa, i.e., the formulation is sprayed directly onto the tissue under the patient's tongue.

In some demonstrative embodiments, the composition of the present invention may be administered in any suitable form for sublingual administration, including but not limited to, sublingual tablets, for example, any tablets which may easily melt in the mouth, dissolve rapidly and with little or no residue; multi-purpose tablets, e.g, soluble tablets for either oral or sublingual (or buccal) administration; sublingual drops, e.g., a concentrated solution and/or a liquid form of the composition of the present invention adapted to be dropped under the tongue; sublingual spray; lozenges, e.g, which may effect a metered and patient-controlled-rate combination of sublingual, buccal, and oral administration; effervescent buccal or sublingual tablets; bioadhesive sublingual tablets; dissolving films According to some embodiments, the preferred administration form may be a sublingual spray.

According to some demonstrative embodiments, the composition of the present invention may be formulated in the form of a dissolving sublingual tablet.

According to some embodiments, the tablet may be prepared using a compression molding process and the tablet may exhibit rapid disintegration and dissolution, which is usually within 5-10 seconds.

In some demonstrative embodiments, the tablet (whether for sublingual or oral administration) may be prepared using direct compression. According to some embodiments, the direct compression method may employ ingredients that can be mixed well and do not require further granulation steps prior to lubrication and compression.

The directly compressible tablet formulation may contain directly compressible soluble excipients, a super disintegrant, and lubricant. According to some embodiments, the formulation may also include microcrystalline cellulose, dry binder, buffers, surface-active agents, sweeteners, and flavors. Sugar-based excipients may also be used in the formulation as bulking agents because of their high aqueous solubility, sweetness, pleasant feeling in the mouth, and good taste-masking.

According to some demonstrative embodiments, the composition may be administered in a tablet or capsule form which may include a substrate comprising the active ingredient covered with at least one enteric coating.

According to some embodiments, the enteric coating may provide protection upon exposure of the composition to the acidic conditions of the stomach, and may dissolve when the composition is further digested throughout the Gastrointestinal (GI) tract, e.g., when reaching the small intestine.

Non-limiting examples of enteric coatings, may include suitable polymers such as cellulose acetate phthalate (CAP); hydroxypropyl methylcellulose phthalate (HPMCP); polyvinyl acetate phthalate; cellulose acetate trimellitate; poly ((methacrylic acid, methyl methacrylate)1:1) (Eudragit L100™), poly((methacrylic acid, ethyl acrylate)1:1) (Eudragit L30D-55) or Eudragit L100-55™, (poly(methacrylic acid, methyl methacrylate)1:2) Eudragit™ S hydroxypropyl methylcellulose acetate succinate (HPMCAS), sodium alginate, and alginic acid or mixtures thereof.

According to some demonstrative embodiments, the present invention provides for granular compositions.

According to some embodiments, a composition containing the active ingredient may mixed and granulated with a suitable carrier material to form a core part of particles to be coated.

In some embodiments, the granulation process may employ a suitable granulator, or alternatively a fluidized bed. The drying process may comprise lyophilization. The granules according to the invention may have a wide range of dimensions. A non-limiting example of a granule according to the invention is an essentially spherical particle having a mean diameter of about from 0.1 to about 1000 microns.

According to some demonstrative embodiments, the enteric coating described herein may comprise one or more pH-sensitive coatings, according to conventional procedures in order to delay the release of the active ingredient. Suitable pH-sensitive polymers include those which are relatively insoluble and impermeable at the pH of the stomach, but which are more soluble or disintegrate or permeable at the pH of the small intestine and colon. Such pH-sensitive polymers include polyacrylamides, phthalate derivatives such as acid phthalate of carbohydrates, amylose acetate phthalate, cellulose acetate phthalate (CAP), other cellulose ester phthalates, cellulose ether phthalates, hydroxypropylcellulose phthalate (HPCP), hydroxypropylethyl cellulose phthalate (HPECP), hydroxylpro-plymethylcellulose phthalate (HPMCP), HPMCAS, methylcellulose phthalate (MCP), polyvinyl acetate phthalate (PVAcP), polyvinyl acetate hydrogen phthalate, sodium CAP, starch acid phthalate, cellulose acetate trimellitate (CAT), styrene-maleic acid dibutyl phthalate copolymer, styrene-maleic acid/polyvinylacetate phthalate copolymer, styrene and maleic acid copolymers, polyacrylic acid derivatives such as acrylic acid and acrylic ester copolymers, polymethacrylic acid and esters thereof, polyacrylic and methacrylic acid copolymers, shellac, and vinyl acetate and crotonic acid copolymers. Preferred pH-sensitive polymers include shellac, phthalate derivatives, CAT, HPMCAS, polyacrylic acid derivatives, particularly copolymers comprising acrylic acid and at least one acrylic acid ester, polymethyl methacrylate blended with acrylic acid and acrylic ester copolymers, and vinyl acetate, crotonic acid copolymers, alginic acid and alginates such as ammonia alginate, sodium, potassium, magnesium or calcium alginate. A particularly preferred group of pH-sensitive polymers includes CAP, PVAcP, HPMCP, HPMCAS, anionic acrylic copolymers of methacrylic acid and methylmethacrylate, and osmopolymers comprising acrylic acid and at least one acrylic acid ester. Cellulose acetate phthalate may be applied as an enteric coating to the encapsulated pro-biotic compositions of the invention to provide delayed release of the active ingredient until the dosage form has exited the stomach. The CAP coating solution may also contain one or more plasticizers, such as diethyl phthalate, polyethyleneglycol-400, triacetin, triacetin citrate, propylene glycol, and others as known in the art. Preferred plasticizers are diethyl phthalate and triacetin. The CAP coating formulation may also contain one or more emulsifiers, such as polysorbate-80. Anionic acrylic copolymers of methacrylic acid and methylmethacrylate are also particularly useful enteric coating materials for delaying the release of the active ingredient until they have moved to a position in the GI tract which is distal to the stomach. Copolymers of this type may include anionic copolymers of methacrylic acid and methylmethacrylate. Preferred non-pH-sensitive aqueous insoluble polymers may include cellulose esters, cellulose ethers, polyacrylates, polyamides, polyesters, and vinyl polymers. Preferred non-pH-sensitive aqueous-soluble polymers include hydroxyalkyl-substituted cellulosics such as HPC, HEC and HPMC, PVA, PEG, PEO, PEG/PPG copolymers, and aqueous-soluble polyamides, polysaccharides, and polyacrylates.

Various additives may be included in such coatings, including emulsifiers, plasticizers, surfactants, fillers and buffers. Finally, the polymeric coating may be described as being "quasi-enteric" in the sense that it remains substantially intact for a significant period of time (e.g., greater than an hour) after the dosage form exits the stomach, thereafter becoming sufficiently permeable to permit gradual release of the active ingredient and diffusion through the coating.

Optionally and preferably, the substrate is an active core for containing the active ingredient, such as, for example, a pellet, a bead or a tablet.

Optionally and preferably, the active core is a tablet formed by compression.

In some demonstrative embodiments, the substrate may further comprise a filler, such as, for example, one or more of microcrystalline cellulose, sodium carboxymethycellulose, ethylcellulose, cellulose acetate, starch, lactose, glucose, fructose, sucrose, dicalcium phosphate, sorbitol, mannitol, mantitol, lactitol, xylitol, isomalt, erythritol, and hydrogenated starch hydrolysates, or a mixture thereof.

In some demonstrative embodiments, the substrate may further comprise a disintegrant, such as, for example, one or more of low-substituted carboxymethyl cellulose sodium, cross-linked polyvinyl pyrrolidone, sodium starch glycolate, cross-linked sodium carboxymethyl cellulose, pregelatinized starch, microcrystalline starch, water insoluble starch, calcium carboxymethyl cellulose, and low substituted hydroxypropyl cellulose magnesium aluminum silicate, or a mixture thereof.

Example 3—Additional Validation of Three Molecules

The activating effect of three compounds (ChemDiv ID E677-1326, E677-0945 and D715-0284) for SIRT6 was validated by conducting the following secondary assays. As previously described, D715-0284 is a stereoisomer of molecule 768382-41-8.

1. HPLC deacylation assay. SIRT6 was incubated with compounds and myristoyl-lysine peptide (corresponding to TNF-alpha sequence) at 37° C. The deacylation reactions were analyzed by reversed phase high-performance liquid chromatography on Kinetex C18 column by monitoring the formation of the deacylated product at 214 nm. The results are shown in FIG. 1, which shows the area under the peak corresponding to the deacylated product. Equally diluted DMSO served as control.

Figure 2:
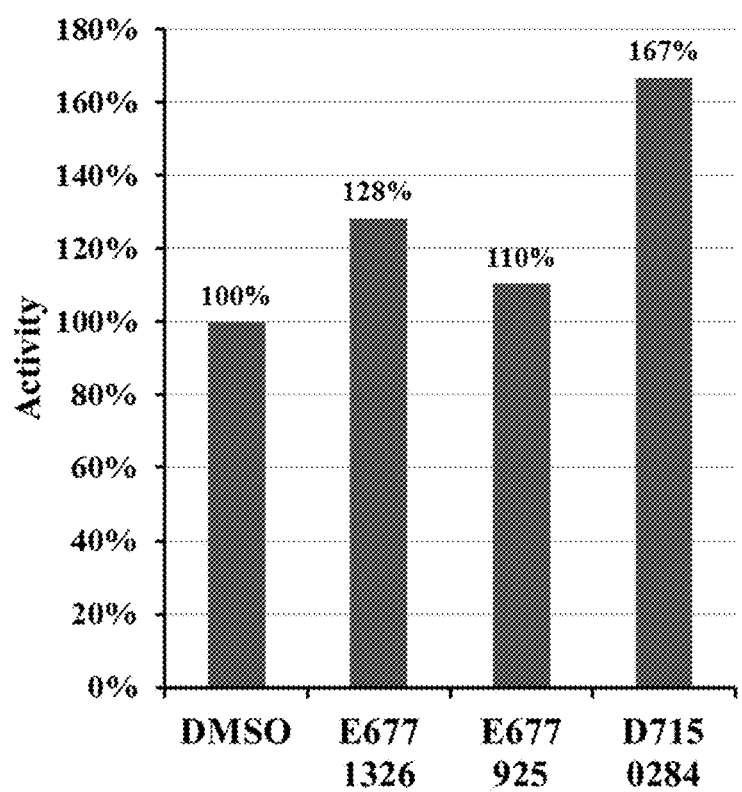
FIG. 2 shows the effect of compounds on SIRT6 deacetylation activity.

2. Fluorometric deacetylation assay. SIRT6 was incubated with compounds and fluorophore-labelled acetyl-lysine peptide (corresponding to histone H3 sequence) at 37° C. FIG. 2 shows the effect of compounds on SIRT6 deacetylation activity. Results are expressed as a percentage of DMSO—treated control.

Figure 3:
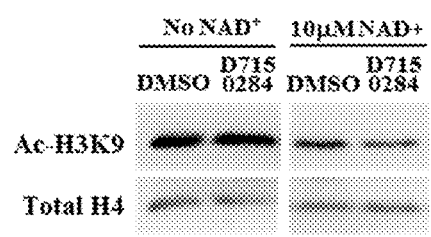
FIG. 3 shows deacetylation of H3K9 on chromatin histones by SIRT6, in the presence or absence of compound D715-0284.

3. In vitro histone deacetylation assay. Chromatin was purified from HEK293T cells by two steps of lysis (with Nonidet P-40 lysis buffer). SIRT6 was incubated with chromatin proteins and the reaction mixture is then used for Western blot analysis. FIG. 3 shows deacetylation of H3K9 on chromatin histones by SIRT6, in the presence or absence of compound D715-0284. SIRT6 (0.5 µM) was incubated with chromatin fractions isolated from HEK293T cells in the presence of 10 micromolar NAD+ and compound D715-0284 or DMSO (control) at 37° C.

Example 4—Initial Pharmacophore Analysis

An initial pharmacophore analysis was performed with the Biovia Discovery Studio package (DASSAULT SYSTEMES, USA) for three compounds, E677-1326, E677-0945 and D715-0284. As previously described, D715-0284 is a stereoisomer of molecule 768382-41-8.

The pharmacophores were determined for the ligands, and may optionally be generalized to describe a group of compounds as follows, including feature definitions which correspond to the data described below and in the corresponding Figures.

Pharmacophore interpretation may optionally be described as follows, such that each compound may optionally be described as: a compound having biological activity as an activator of SIRT6, which compound binds to SIRT6 as an activator, and having at least five chemical functionalities for interacting with SIRT6, wherein said functionalities provide a pharmacophoric motif selected from the group consisting of:

MOTIF 1 Charged Positive, Ring Aromatic, HBAcceptor, Charged Positive, Ring Aromatic MOTIF 2 Charged Positive, HBAcceptor, Ring Aromatic, Ring Aromatic, HBAcceptor, HBAcceptor MOTIF 3 Charged Positive, Hydrophobe Aromatic, HBAcceptor, Ring Aromatic, HBAcceptor MOTIF 4 Hydrophobe, HBAcceptor, HBDonor, HBAcceptor, HBDonor MOTIF 5 Hydrophobe, HBAcceptor, Ring Aromatic, HBDonor, HBDonor wherein;

a HYDROPHOBE feature is defined as a contiguous set of atoms that are not adjacent to any concentrations of charge (charged atoms or electronegative atoms), in a conformation such that the atoms have surface accessibility;

a HYDROPHOBE AROMATIC feature is defined as a contiguous set of atoms that are not adjacent to any concentrations of charge (charged atoms or electronegative atoms), in a conformation such that the atoms have surface accessibility, arranged as an aromatic, including moieties selected from the group consisting of neutral homocyclics, heterocyclics, fused aromatics, polycyclics and substituted aromatics;

a CHARGED POSITIVE feature is defined as atoms or groups of atoms that are likely to be protonated at physiological pH;

a RING AROMATIC feature is defined as a contiguous set of atoms, in a ring conformation wherein the atoms have surface accessibility, including moieties selected from the group consisting of neutral homocyclics, heterocyclics, fused aromatics, polycyclics and substituted aromatics;

a HBDONOR feature is defined as a moiety that acts as a hydrogen bond donor;

and a HBACCEPTOR feature is defined as a moiety that acts as a hydrogen bond acceptor;

and wherein:

(a) a pharmacophore consisting of at least the following chemical features can be used to describe MOTIF 1:

Two Charged Positive features, two Ring Aromatic features and a HBAcceptor, in which each feature is represented by a sphere of 1.6 Angstroms;

The positions of each feature are described as follows:

Charged Positive 1 has Cartesian XYZ co-ordinates of 2.473, 2.595, −0.526

Charged Positive 2 has co-ordinates of −2.782, 0.903, −0.968

Ring Aromatic 1 has co-ordinates of 3.692, 4.171, 1.434

Ring Aromatic 2 has co-ordinates of −1.784, −3.852, 1.181

Figure 4A:
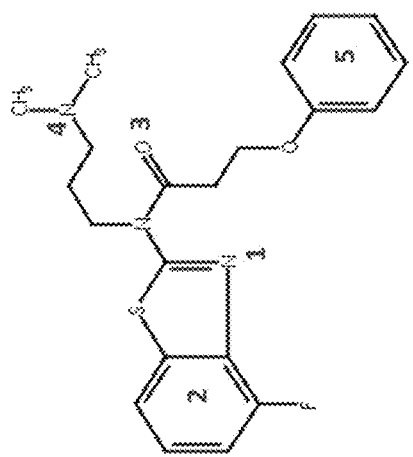
FIGS. 4A-4E show exemplary pharmacophores for E677-1326, E677-0945 and D715-0284.
Figure 4A:
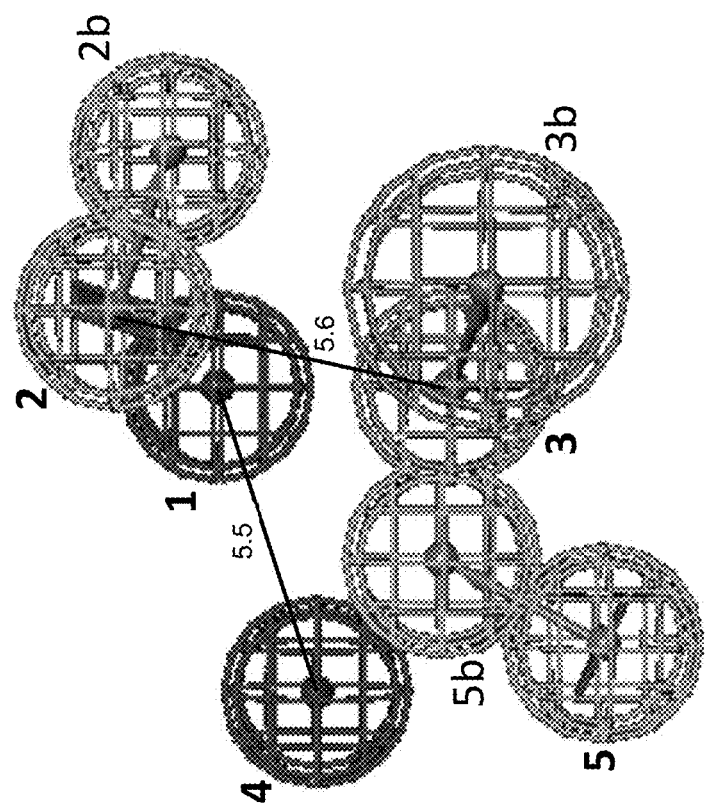

HBAcceptor has co-ordinates of 2.468−1.358 0.921 and the distance and angle constraints for these are shown in FIG. 4A;

and wherein:

(b) a pharmacophore consisting of at least the following chemical features can be used to describe MOTIF 2:

A Charged Positive feature, three HBAcceptor features and two Ring Aromatic features, in which each feature is represented by a sphere of 1.6 Angstroms;

The positions of each feature are described as follows:

Charged Positive has Cartesian XYZ co-ordinates of −3.757, 3.438, −0.387

HBAcceptor 1 has Cartesian XYZ co-ordinates of 1.508, 5.105, −2.536

HBAcceptor 2 has Cartesian XYZ co-ordinates of −1.511, −1.486, 0.075

HBAcceptor 3 has Cartesian XYZ co-ordinates of 2.258, 0.942, 0.179

Ring Aromatic 1 has co-ordinates of 3.224, 3.61, −1.004

Figure 4B:
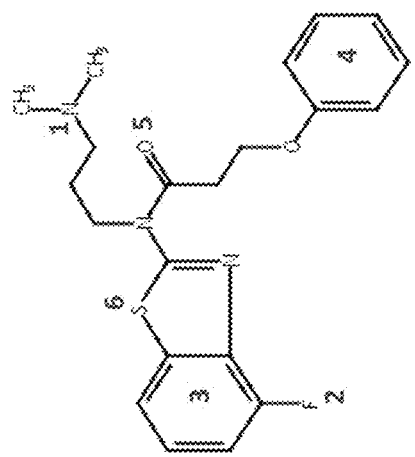
Figure 4B:
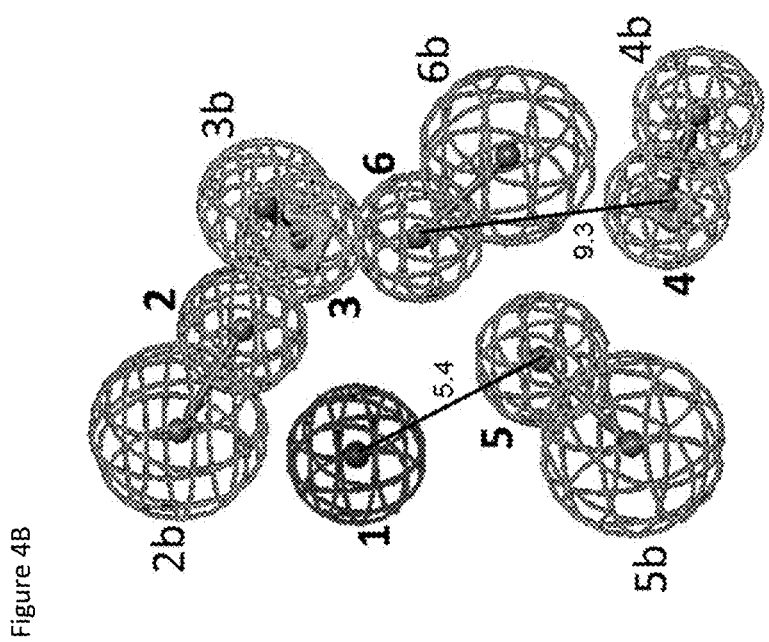

Ring Aromatic 2 has co-ordinates of 2.645, −5.558, 0.909 and the distance and angle constraints for these are shown in FIG. 4B;

and wherein:

(c) a pharmacophore consisting of at least the following chemical features can be used to describe MOTIF 3:

A Charged Positive feature, two HBAcceptor features, a Hydrophobe Aromatic feature and a Ring Aromatic feature, in which each feature is represented by a sphere of 1.6 Angstroms;

The positions of each feature are described as follows:

Charged Positive has Cartesian XYZ co-ordinates of −1.373, 1.99, −1.36

HBAcceptor 1 has Cartesian XYZ co-ordinates of 2.714, −1.935, 1.105

HBAcceptor 2 has Cartesian XYZ co-ordinates of −0.84, −3.379, 0.729

Hydrophobe Aromatic has Cartesian XYZ co-ordinates of −3.134, −4.648, 1.579

Figure 4C:
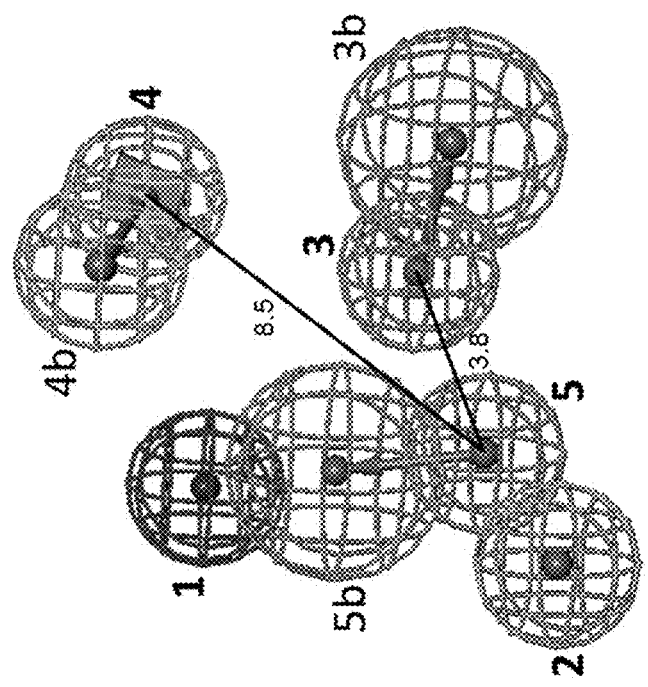

Ring Aromatic has Cartesian XYZ co-ordinates of 4.051, 3.593, 0.723 and the distance and angle constraints for these are shown in FIG. 4C;

and wherein (d) a pharmacophore consisting of at least the following chemical features can be used to describe MOTIF 4:

A Hydrophobe feature, two HBAcceptor features, and two HBDonor features, in which each feature is represented by a sphere of 1.6 Angstroms;

The positions of each feature are described as follows:

Hydrophobe has Cartesian XYZ co-ordinates of 3.702, 4.163, −1.853

HBAcceptor 1 has Cartesian XYZ co-ordinates of −0.406, 4.241, −2.227

HBAcceptor 2 has Cartesian XYZ co-ordinates of −3.403, −3.629, 3.275

HBDonor 1 has Cartesian XYZ co-ordinates of −3.403, −3.629, 3.275

Figure 4D:
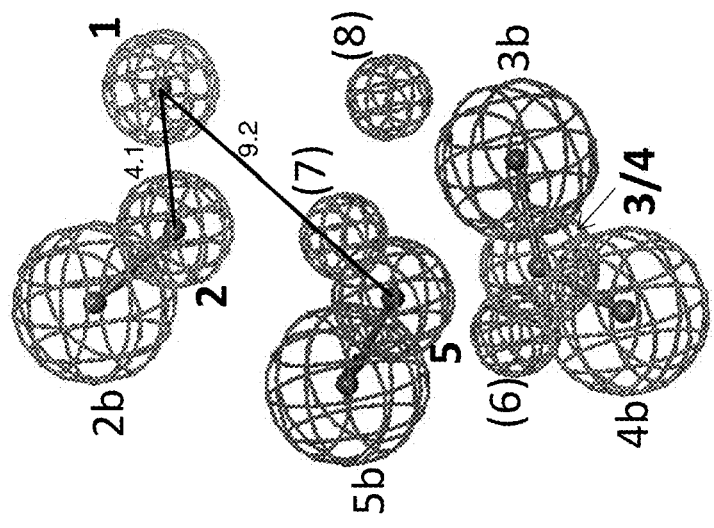

HBDonor 2 has Cartesian XYZ co-ordinates of −3.852, 0.454, 2.037 and the distance and angle constraints for these are shown in FIG. 4D;

and wherein (e) a pharmacophore consisting of at least the following chemical features can be used to describe MOTIF 5:

A Hydrophobe feature, A HBAcceptor feature, a Ring Aromatic feature and two to HBDonor features, in which each feature is represented by a sphere of 1.6 Angstroms;

The positions of each feature are described as follows:

Hydrophobe has Cartesian XYZ co-ordinates of 3.702, 4.163, −1.853

HBAcceptor has Cartesian XYZ co-ordinates of −0.406, 4.241, −2.227

Ring Aromatic has Cartesian XYZ co-ordinates of 1.288, 0.12, −0.338

HBDonor 1 has Cartesian XYZ co-ordinates of −3.403, −3.629, 3.275

Figure 4E:
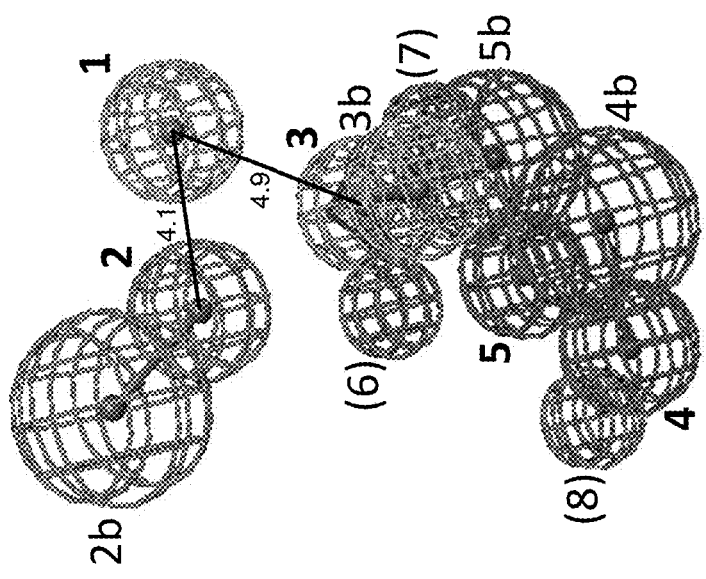

HBDonor 2 has Cartesian XYZ co-ordinates of −0.925, −4.787, −0.207 and the distance and angle constraints for these are shown in FIG. 4E.

Preferably the compound induces SIRT6 catalyzed deacylation or deacetylation.

The results are shown in FIGS. 4A-4E, each of which features the pharmacophore for the ligand on the left, with numbered features; and the ligand on the right, with the corresponding parts of the ligand numbered, to show correspondence to the numbered pharmacophore features. Colors shown are described in the tables below, to further aid identification.

A "centroid" is a feature that is determined by a surface model, such as of a ring aromatic (the ring aromatic vector is a "ring aromatic normal").

Hydrogen bond donors (HBDonor) and acceptors (HBAcceptors) are shown with "tail" and "head" portions of the moiety labeled.

An "exclusion sphere" relates to the volume of space from which other parts of the ligand are excluded. The "excluded volume" relates to areas excluded by the ligand.

FIGS. 4A and 4B relate to exemplary pharmacophores for E677-1326.

For FIG. 4A, Table 4A shows a description of the type, coordinates and radius for each feature, plus color coordination information. Table 4B shows the relative distance between each feature.

TABLE 4A

| # | Type | Color | X | Y | Z | Radius |
|---|---|---|---|---|---|---|
| 1 | Charged_Positive | | 2.473 | 2.595 | −0.526 | 1.6 |
| 2 | Ring_Aromatic_Centroid | | 3.692 | 4.171 | 1.434 | 1.6 |
| 2b | Ring_Aromatic_Normal | | 6.39728 | 3.36792 | 0.4159 | 1.6 |
| 3 | HBAcceptor_Tail | | 2.468 | −1.358 | 0.921 | 1.6 |
| 3b | HBAcceptor_Head | | 3.98 | −1.827 | 3.469 | 2.2 |
| 4 | Charged_Positive | | −2.782 | 0.903 | −0.968 | 1.6 |
| 5 | Ring_Aromatic_Centroid | | −1.784 | −3.852 | 1.181 | 1.6 |
| 5b | Ring_Aromatic_Normal | | −0.4093 | −1.1955 | 0.95005 | 1.6 |

TABLE 4B

| Feature | Distance | | | |
|---|---|---|---|---|
| # | 2 | 3 | 4 | 5 |
| 1 | 2.706 | 4.21 | 55.38 | 7.912 |
| 2 | | 5.686 | 7.64 | 9.717 |
| 3 | | | 6.02 | 4.936 |
| 4 | | | | 5.313 |

For FIG. 4B, Table 5A shows a description of the type, coordinates and radius for each feature, plus color coordination information. Table 5B shows the relative distances between each feature.

TABLE 5A

| # | Type | Color | X | Y | Z | Radius |
|---|---|---|---|---|---|---|
| 1 | Charged Positive | | −3.757 | 3.438 | 0.387 | 1.6 |
| 2 | HBAcceptor_Tail | | 1.508 | 5.105 | −2.536 | 1.6 |
| 2b | HBAcceptor_Head | | −0.382 | 6.736 | −4.199 | 2.2 |
| 3 | Ring_Aromatic_Centroid | | 3.224 | 3.61 | −1.004 | 1.6 |
| 3b | Ring_Aromatic_Normal | | 2.23718 | 5.03675 | 1.44356 | 1.6 |
| 4 | Ring_Aromatic_Centroid | | 2.645 | −5.558 | 0.909 | 1.6 |
| 4b | Ring_Aromatic_Normal | | 3.08508 | −5.558 | 3.87655 | 1.6 |
| 5 | HBAcceptor_Tail | | −1.511 | −1.486 | 0.075 | 1.6 |
| 5b | HBAcceptor_Head | | −3.864 | −3.322 | −0.232 | 2.2 |
| 6 | HBAcceptor_Tail | | 2.258 | 0.942 | 0.179 | 1.6 |
| 6b | HBAcceptor_Head | | 3.358 | −1.195 | 1.975 | 2.2 |

TABLE 5B

| Feature | Distance | | | | |
|---|---|---|---|---|---|
| # | 2 | 3 | 4 | 5 | 6 |
| 1 | 5.926 | 7.01 | 11.117 | 5.432 | 6.537 |
| 2 | | 2.743 | 11.263 | 7.705 | 5.026 |
| 3 | | | 9.383 | 7.646 | 4.286 |
| 4 | | | | 5.878 | 6.552 |
| 5 | | | | | 4.485 |

FIG. 4C shows an exemplary pharmacophore for E677-0945. For FIG. 4C, Table 6A shows a description of the type, coordinates and radius for each feature, plus color coordination information. Table 6B shows the relative distances between each feature.

TABLE 6A

| # | Type | Color | X | Y | Z | Radius |
|---|---|---|---|---|---|---|
| 1 | Charged_Positive | | −1.373 | 1.99 | −1.36 | 1.6 |
| 2 | Hydrophobe_Aromatic | | −3.134 | −4.648 | 1.579 | 1.6 |
| 3 | HBAcceptor_Tail | | 2.714 | −1.935 | 1.105 | 1.6 |
| 3b | HBAcceptor_Head | | 4.618 | −2.18 | 3.41 | 2.2 |
| 4 | Ring_Atomic_Centroid | | 4.051 | 3.593 | 0.723 | 1.6 |
| 4b | Ring_Aromatic_Normal | | 1.93713 | 4.39995 | 2.69287 | 1.6 |
| 5 | HBAcceptor_Tail | | −0.84 | −3.379 | 0.729 | 1.6 |
| 5b | HBAcceptor-Head | | −1.161 | −0.516 | −0.108 | 2.2 |

TABLE 6B

| Feature # | Distance | | | |
|---|---|---|---|---|
| | 2 | 3 | 4 | 5 |
| 1 | 7.470 | 6.179 | 6.027 | 5.786 |
| 2 | | 6.464 | 10.967 | 2.756 |
| 3 | | | 5.700 | 3.855 |
| 4 | | | | 8.516 |

FIGS. 4D and 4E show exemplary pharmacophores for D715-0284. For FIG. 4D, Table 7A shows a description of the type, coordinates and radius for each feature, plus color coordination information. Table 7B shows the relative distances between each feature.

TABLE 7A

| # | Type | Color | X | Y | Z | Radius |
|---|---|---|---|---|---|---|
| 1 | Hydrophobe | | 3.702 | 4.163 | −1.853 | 1.6 |
| 2 | HBAcceptor_Tail | | −0.406 | 4.241 | −2.227 | 1.6 |
| 2b | HBAcceptor_Head | | −2.138 | 6.445 | −3.297 | 2.2 |
| 3 | HBDonor_Tail | | −3.403 | −3.629 | 3.275 | 1.6 |
| 3b | HBDonor_Head | | −0.446 | −3.31 | 3.671 | 2.2 |
| 4 | HBAcceptor_Tail | | −3.403 | −3.629 | 3.275 | 1.6 |
| 4b | HBAcceptor_Head | | −5.373 | −4.381 | 5.409 | 2.2 |
| 5 | HBDonor_Tail | | −3.852 | 0.454 | 2.037 | 1.6 |
| 5b | HBDonor_Head | | −5.458 | 0.707 | −0.484 | 2.2 |
| (6) | ExclusiveSphere | | −4.799 | −3.511 | 1.826 | 1.2 |
| (7) | ExcludedVolume_1.11 | | −1.194 | −0.064 | −0.486 | 1.2 |
| (8) | ExcludedVolume_1.12 | | 2.653 | −1.743 | 0.59 | 1.2 |

TABLE 7B

| Feature # | Distance | | | |
|---|---|---|---|---|
| | 2 | 3 | 4 | 5 |
| 1 | 4.126 | 11.726 | 11.726 | 9.271 |
| 2 | | 10.059 | 10.059 | 6.663 |
| 3 | | | — | 4.290 |
| 4 | | | | 4.290 |

For FIG. 4E, Table 8A shows a description of the type, coordinates and radius for each feature, plus color coordination information. Table 8B shows the relative distances between each feature.

TABLE 8A

| # | Type | Color | X | Y | Z | Radius |
|---|---|---|---|---|---|---|
| 1 | Hydrophobe | | 3.702 | 4.163 | −1.853 | 1.6 |
| 2 | HBAcceptor_Tail | | −0.406 | 4.241 | −2.227 | 1.6 |
| 2b | HBAcceptor_Head | | −2.138 | 6.445 | −3.297 | 2.2 |
| 3 | Ring_Aromatic_Centroid | | 1.288 | 0.12 | −0.338 | 1.6 |
| 3b | Ring_Aromatic_Normal | | 1.03402 | 1.29691 | 2.40979 | 1.6 |
| 4 | HBDonor_Tail | | −3.403 | −3.629 | 3.275 | 1.6 |
| 4b | HBDonor_Head | | −0.446 | −3.31 | 3.671 | 2.2 |
| 5 | HBDonor_Tail | | −0.925 | −4.787 | −0.207 | 1.6 |
| 5b | HBDonor_Head | | 2.06 | −4.549 | −0.025 | 2.2 |
| (6) | ExclusiveSphere | | −1.194 | −0.064 | −0.486 | 1.2 |
| (7) | ExcludedVolume_1.11 | | 2.653 | −1.743 | 0.59 | 1.2 |
| (8) | ExcludedVolume_1.12 | | −4.799 | −3.511 | 1.826 | 1.2 |

TABLE 8B

| Feature # | Distance | | | |
|---|---|---|---|---|
| | 2 | 3 | 4 | 5 |
| 1 | 4.126 | 4.947 | 11.726 | 10.209 |
| 2 | | 4.839 | 10.059 | 9.266 |
| 3 | | | 7.008 | 5.385 |
| 4 | | | | 4.428 |

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of a treatment with a SIRT6 activator, for a subject in need of treatment thereof, comprising administering a compound selected from the group consisting of:

A

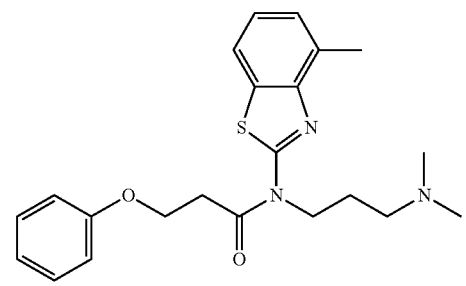 [SMILES: CN(C)CCCN(C(=O)CCOc1ccccc1)c1nc2c(F)cccc2s1]

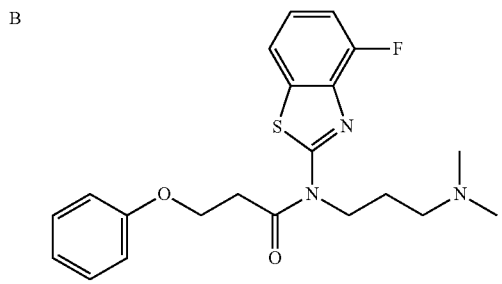
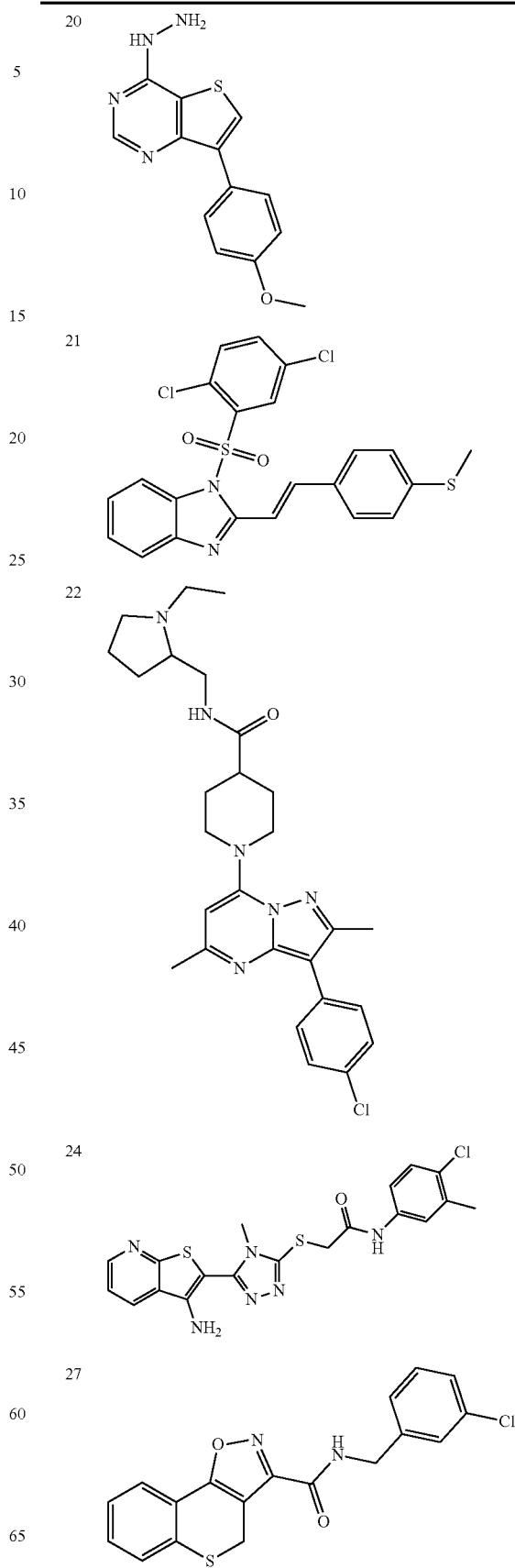

28 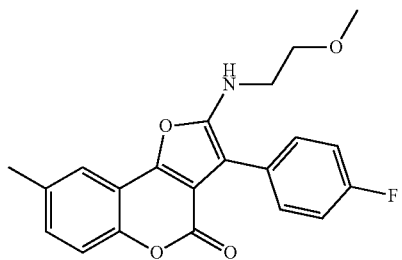 [SMILES: COCCNc1oc2c(c1-c1ccc(F)cc1)c(=O)oc1ccc(C)cc12]
29 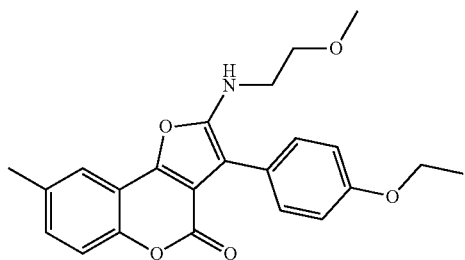 [SMILES: CCOc1ccc(-c2c(NCCOC)oc3c2c(=O)oc2ccc(C)cc23)cc1]
30 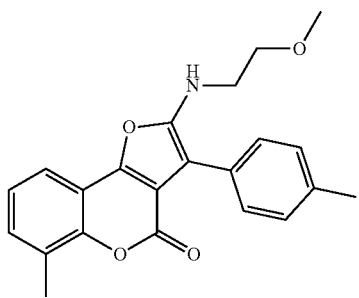 [SMILES: COCCNc1oc2c(c1-c1ccc(C)cc1)c(=O)oc1c(C)cccc12]
35 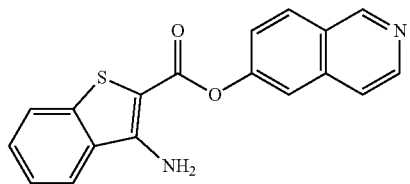 [SMILES: Nc1c(C(=O)Oc2ccc3cnccc3c2)sc2ccccc12]
36 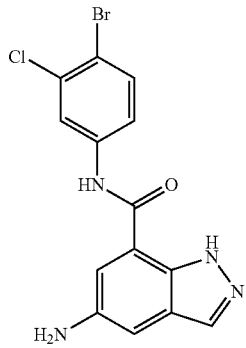 [SMILES: Nc1cc(C(=O)Nc2ccc(Br)c(Cl)c2)c2[nH]ncc2c1]
39 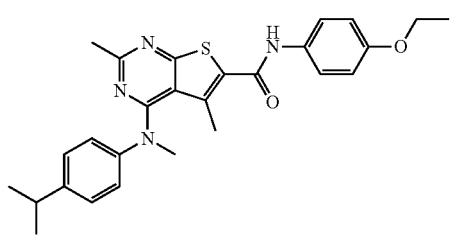 [SMILES: CCOc1ccc(NC(=O)c2sc3nc(C)nc(N(C)c4ccc(C(C)C)cc4)c3c2C)cc1]
50 
51 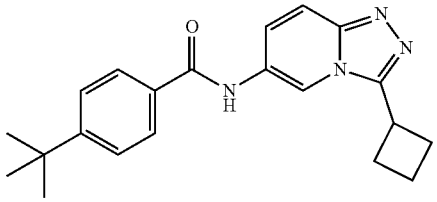 [SMILES: CC(C)(C)c1ccc(C(=O)Nc2ccc3nnc(C4CCC4)n3c2)cc1]
52 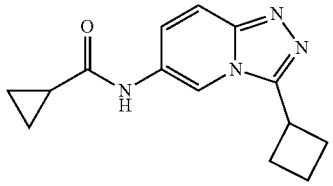 [SMILES: O=C(Nc1ccc2nnc(C3CCC3)n2c1)C1CC1]
55 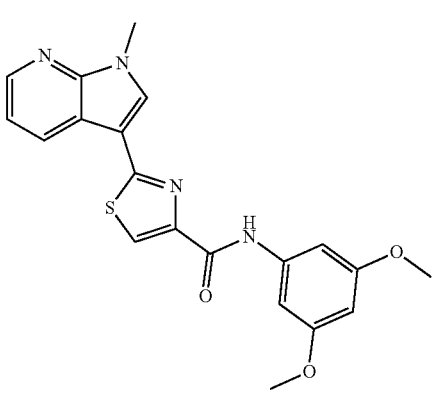 [SMILES: COc1cc(NC(=O)c2csc(-c3cn(C)c4ncccc34)n2)cc(OC)c1]
56 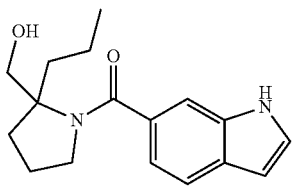 [SMILES: CCCC1(CO)CCCN1C(=O)c1ccc2cc[nH]c2c1]
57 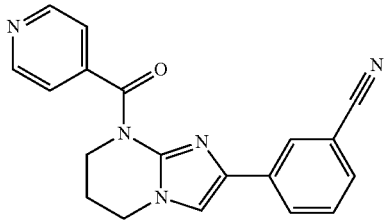 [SMILES: N#Cc1cccc(-c2cn3c(n2)N(C(=O)c2ccncc2)CCC3)c1]

58

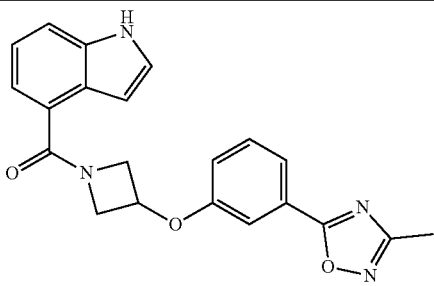

63

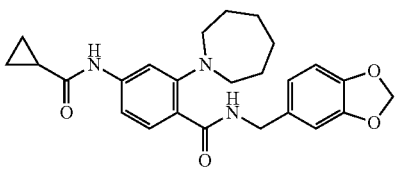 [SMILES: O=C(NCc1ccc2c(c1)OCO2)c1ccc(NC(=O)C2CC2)cc1N1CCCCCC1]

64

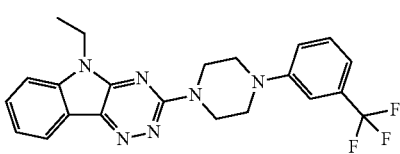 [SMILES: CCn1c2ccccc2c2nnc(N3CCN(c4cccc(C(F)(F)F)c4)CC3)nc21]

to the subject.

2. The method of claim 1, wherein the compound is selected from the group consisting of A and B.

3. The method of claim 2, wherein the subject is suffering from a condition amenable to treatment with the SIRT6 activator and wherein the condition is selected from the group consisting of obesity, an obesity-related disease, and a fat-related metabolic disorder.

4. The method of claim 2, wherein the subject is suffering from a condition selected from the group consisting of lipid disorders including hyperlipidemia and hyperuricemia, insulin resistance, noninsulin dependent diabetes mellitus (NIDDM, or Type II diabetes), insulin dependent diabetes mellitus (IDDM or Type I diabetes), diabetes-related complications including microangiopathic lesions, ocular lesions, retinopathy, neuropathy, and renal lesions, cardiovascular disease (including cardiac insufficiency, coronary insufficiency, and high blood pressure), atherosclerosis, atheromatous disease, stroke, hypertension, Syndrome X, gallbladder disease, osteoarthritis, sleep apnea, uterine cancer, breast cancer, colorectal cancer, kidney cancer, and gallbladder cancer, high cholesterol levels, complications of pregnancy, menstrual irregularities, hirsutism, muscular dystrophy, infertility, a weight-related disorder and increased surgical risk.

5. The method of claim 2, wherein the subject is suffering from a condition amenable to treatment with the SIRT6 activator and wherein the subject has a body fat percentage of at least at 20%.

6. The method of claim 2, wherein the subject is suffering from a condition amenable to treatment with the SIRT6 activator and wherein the condition is selected from the group consisting of type 2 diabetes, prediabetes, glucose intolerance, insulin insensitivity, hyperglycemia, hypoglycemia, gestational diabetes, drug-induced diabetes; overweight, obesity, high percent body fat and/or body composition and/or body fat location, dyslipidemia defined as abnormal levels of blood lipids; and non-alcoholic fatty liver disease (NAFLD).

7. The method of claim 2, wherein the subject is suffering from a condition amenable to treatment with the SIRT6 activator and wherein the condition is selected from the group consisting of cardiovascular disease, neurodegenerative disease, premature aging syndrome and aging.

8. The method of claim 2, wherein the subject is suffering from a condition amenable to treatment with the SIRT6 activator and wherein the condition is selected from the group consisting of breast cancer, cervical cancer, ovary cancer, endometrial cancer, melanoma, uveal melanoma, bladder cancer, lung cancer, pancreatic cancer, colorectal cancer, prostate cancer, leukemia, acute lymphocytic leukemia, chronic lymphocytic leukemia, B-cell lymphoma, Burkitt's lymphoma, multiple myeloma, Non-Hodgkin's lymphoma, myeloid leukemia, acute myelogenous leukemia (AML), chronic myelogenous leukemia, thyroid cancer, thyroid follicular cancer, myelodysplastic syndrome (MDS), fibrosarcomas and rhabdomyosarcomas, teratocarcinoma, neuroblastoma, glioma, glioblastoma, benign tumor of the skin, keratoacanthomas, renal cancer, anaplastic large-cell lymphoma, esophageal cancer, follicular dendritic cell carcinoma, seminal vesicle tumor, epidermal carcinoma, spleen cancer, bladder cancer, head and neck cancer, stomach cancer, liver cancer, bone cancer, brain cancer, cancer of the retina, biliary cancer, small bowel cancer, salivary gland cancer, cancer of uterus, cancer of testicles, cancer of connective tissue, myelodysplasia, Waldenstrom's macroglobinaemia, nasopharyngeal, neuroendocrine cancer, mesothelioma, angiosarcoma, Kaposi's sarcoma, carcinoid, fallopian tube cancer, peritoneal cancer, papillary serous mtillerian cancer, malignant ascites, gastrointestinal stromal tumor (GIST), Li-Fraumeni syndrome, and Von Rippel-Lindau syndrome (VHL).

* * * * *